(12) United States Patent
Yaver et al.

(10) Patent No.: US 6,548,274 B2
(45) Date of Patent: Apr. 15, 2003

(54) METHODS FOR PRODUCING A POLYPEPTIDE USING A CRIPPLED TRANSLATIONAL INITIATOR SEQUENCE

(75) Inventors: Debbie S. Yaver, Davis, CA (US); Daniel A. Bellini, Woodland, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/760,139

(22) Filed: Jan. 12, 2001

(65) Prior Publication Data

US 2002/0058304 A1 May 16, 2002

Related U.S. Application Data

(63) Continuation-in-part of application No. 09/482,751, filed on Jan. 13, 2000, now abandoned.

(51) Int. Cl.[7] .................. C12N 15/00; C12N 15/09; C12N 1/20; C12P 21/00; C07H 21/04
(52) U.S. Cl. .................. 435/69.1; 435/69.7; 435/320.1; 435/252; 435/254.1; 435/254.2; 435/254.3; 435/255.1; 536/23.1; 536/23.4; 536/24.1
(58) Field of Search .................. 536/23.1, 23.4, 536/24.1; 435/69.1, 320.1, 252, 254.1, 254.2, 254.3, 255.1, 69.7

(56) References Cited

U.S. PATENT DOCUMENTS 5,578,461 A    11/1996   Sherwin et al.
5,648,267 A  * 7/1997   Reff .................. 435/320.1
5,821,102 A  * 10/1998  Berka et al. .................. 435/198

FOREIGN PATENT DOCUMENTS

WO    WO 94/11523    5/1994

* cited by examiner

*Primary Examiner*—Terry McKelvey
*Assistant Examiner*—Gerald G. Leffers, Jr.
(74) *Attorney, Agent, or Firm*—Robert L. Stames

(57) ABSTRACT

The present invention relates to methods for producing a polypeptide, comprising: (a) cultivating a fungal host cell in a medium conducive for the production of the polypeptide; and (b) isolating the polypeptide from the cultivation medium; wherein the fungal host cell comprises a first nucleic acid sequence encoding the polypeptide in tandem with a second nucleic acid sequence comprising a crippled translational initiator sequence operably linked to a gene encoding a selectable marker, wherein the copy number of the first nucleic acid sequence has been increased by culturing the cell under conditions that select for multiple copies of the selectable marker. The present invention also relates to such fungal host cells and methods for obtaining such fungal host cells. The present invention further relates to nucleic acid constructs and vectors comprising a crippled translational initiator sequence operably linked to a gene encoding a selectable marker.

24 Claims, 11 Drawing Sheets

US 6,548,274 B2

METHODS FOR PRODUCING A POLYPEPTIDE USING A CRIPPLED TRANSLATIONAL INITIATOR SEQUENCE

CROSS-REFERENCE TO RELATED APPLICATION

This application is a continuation-in-part of U.S. application Ser. No. 09/482,751 filed Jan. 13, 2000, now abandoned, which application is fully incorporated herein by reference.

BACKGROUND OF THE INVENTION

1. Field of the Invention

The present invention relates to methods for producing polypeptides involving the use of a crippled translational initiator sequence operably linked to a gene encoding a selectable marker. The present invention also relates to nucleic acid constructs, vectors, and host cells comprising a crippled translational initiator sequence operably linked to a gene encoding a selectable marker.

2. Description of the Related Art

The continual development of new genetic engineering techniques has enabled the manipulation of the expression of genes encoding proteins. The manipulation of the coding region or the transcriptional control regions of a gene has frequently involved the isolation of the gene, manipulation of the nucleic acids contained in the gene in order to increase or decrease expression of the gene, and introduction of the manipulated gene into a suitable expression host.

A widely used method for increasing production of a polypeptide is to obtain a strain with multiple copies of the gene encoding the polypeptide through a process called amplification.

U.S. Pat. No. 5,578,461 discloses the inclusion via homologous recombination of an amplifiable selectable marker gene in tandem with a gene where strains containing amplified copies of the selectable marker in tandem with multiple copies of the gene can be selected for by culturing the strains in the presence of increasing amounts of the appropriate selectable agent.

WO 94/11523 discloses expression vectors comprising a fully impaired yeast Kozak consensus sequence for impairment of translation of a protein encoded by a dominant selectable marker.

It is an object of the present invention to provide improved methods for producing a polypeptide in a fungal host cell using crippled translational initiator sequences.

SUMMARY OF THE INVENTION

The present invention relates to methods for producing a polypeptide, comprising: (a) cultivating a fungal host cell in a medium conducive for the production of the polypeptide; and (b) isolating the polypeptide from the cultivation medium; wherein the fungal host cell comprises a first nucleic acid sequence encoding the polypeptide in tandem with a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, wherein the crippled translational initiator sequence comprises a T at the −3 position and a T at one or more of the −1, −2, and −4 positions, and wherein the copy number of the first nucleic acid sequence has been increased by culturing the cell under conditions that select for multiple copies of the selectable marker.

The present invention also relates to methods for obtaining a fungal host cell for production of a polypeptide, comprising: (a) integrating into the genome of the fungal cell a nucleic acid construct comprising a first nucleic acid sequence encoding the polypeptide in tandem with a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker; and (b) culturing the cell under conditions that select for multiple copies of the selectable marker wherein the copy number of the first nucleic acid sequence is increased, wherein the crippled translational initiator sequence comprises a T at the −3 position and a T at one or more of the −1, −2, and −4 positions.

The present invention also relates to nucleic acid constructs comprising a first nucleic acid sequence encoding the polypeptide in tandem with a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, wherein the crippled translational initiator sequence comprises a T at the −3 position and a T at one or more of the −1, −2, and −4 positions. The present invention further relates to recombinant expression vectors and fungal host cells containing such nucleic acid constructs.

DETAILED DESCRIPTION OF THE INVENTION

Figure 1:
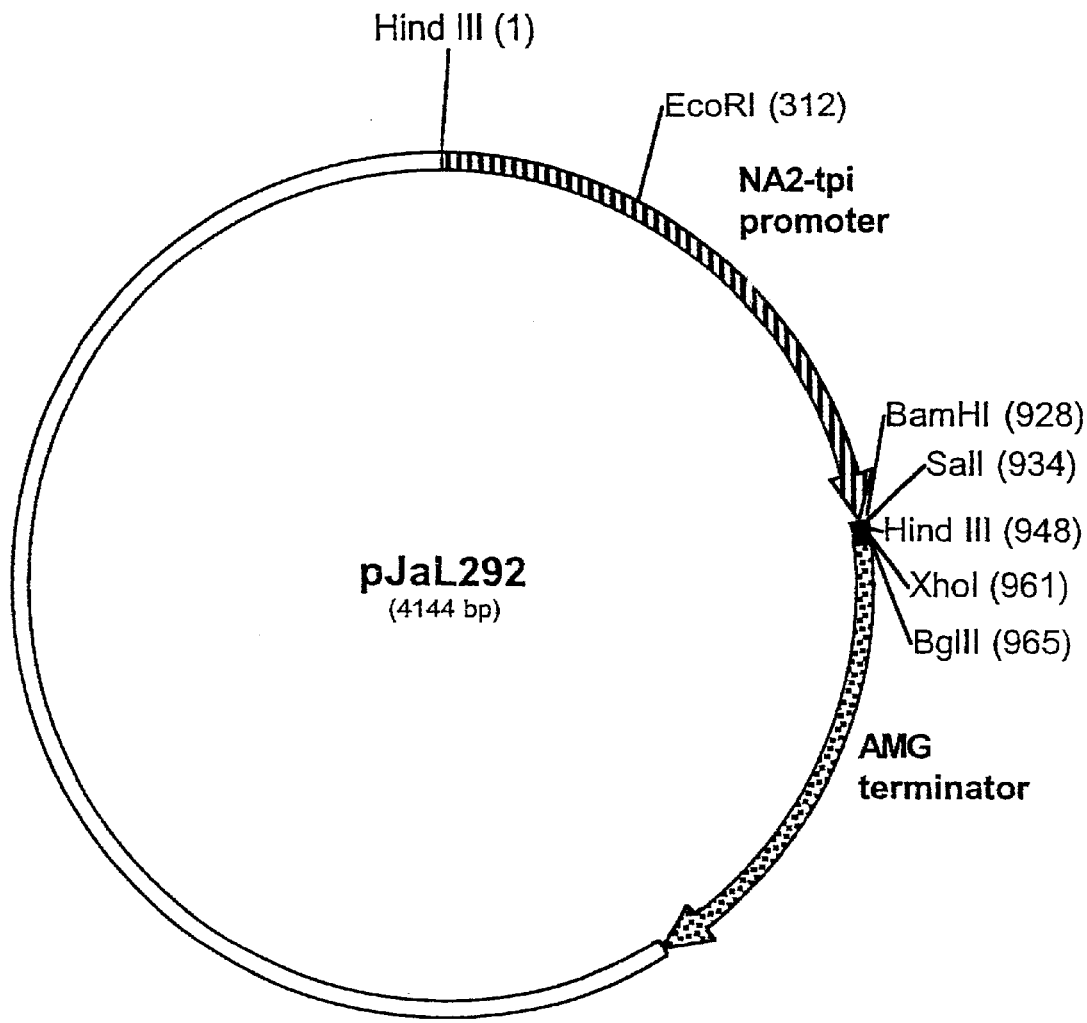
FIG. 1 shows a restriction map of pJaL292.

The present invention relates to methods for producing a polypeptide, comprising: (a) cultivating a fungal host cell in a medium conducive for the production of the polypeptide; and (b) isolating the polypeptide from the cultivation medium; wherein the fungal host cell comprises a first nucleic acid sequence encoding the polypeptide in tandem with a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, and wherein the crippled translational initiator sequence comprises a T at the −3 position and a T at one or more of the −1, −2, and −4 positions. The copy number of the first nucleic acid sequence has been increased by culturing the cell under conditions that select for multiple copies of the selectable marker.

In the production methods of the present invention, the cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate.

In the methods of the present invention, the fungal cell preferably produces at least about 25% more, more preferably at least about 50% more, more preferably at least about 75% more, more preferably at least about 100% more, even more preferably at least about 200% more, most preferably at least about 300% more, and even most preferably at least about 400% more polypeptide relative to a fungal cell comprising a first nucleic acid sequence encoding the polypeptide in tandem with a second nucleic acid sequence comprising a native translational initiator sequence operably linked to a gene encoding a selectable marker when cultured under the same conditions.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J. -C. Janson and Lars Ryden, editors, VCH Publishers, New York, 1989).

Crippled Translational Initiator Sequences

The term "translational initiator sequence" is defined herein as the ten nucleotides immediately upstream of the initiator or start codon of the open reading frame of a polypeptide-encoding nucleic acid sequence. The initiator codon encodes for the amino acid methionine, the so-called "start" codon. The initiator codon is typically an ATG, but may also be any functional start codon such as GTG. It is well known in the art that uracil, U, replaces the deoxynucleotide thymine, T, in RNA.

The term "crippled translational initiator sequence" is defined herein as the ten nucleotides immediately upstream of the initiator codon of the open reading frame of a polypeptide-encoding nucleic acid sequence, wherein the initiator sequence comprises a T at the −3 position and a T at one or more of the −1, −2, and −4 positions.

The term "operably linked" is defined herein as a configuration in which a control sequence, e.g., a crippled translational initiator sequence, is appropriately placed at a position relative to a coding sequence such that the control sequence directs the production of a polypeptide encoded by the coding sequence.

The term "coding sequence" is defined herein as a nucleic acid sequence that is transcribed into mRNA which is translated into a polypeptide when placed under the control of the appropriate control sequences. The boundaries of the coding sequence are generally determined by the start codon located at the beginning of the open reading frame of the 5' end of the mRNA and a stop codon located at the 3' end of the open reading frame of the mRNA. A coding sequence can include, but is not limited to, genomic DNA, cDNA, semisynthetic, synthetic, and recombinant nucleic acid sequences.

In the methods of the present invention, the crippled translational initiator sequence is foreign to the gene encoding a selectable marker.

The crippled translational sequence results in inefficient translation of the gene encoding, the selectable marker. When a fungal host cell, containing an expression cassette comprising a first nucleic acid sequence encoding a polypeptide of interest in tandem with a second nucleic acid sequence comprising a crippled translational initiator sequence operably linked to a gene encoding a selectable marker, is cultured under conditions that select for multiple copies of the selectable marker, the copy number of the polypeptide-encoding nucleic acid sequence is increased.

The term "selectable marker" is defined herein as a gene the product of which provides for biocide or viral resistance, resistance to heavy metals, prototrophy to auxotrophs, and the like, which permits easy selection of transformed cells. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The term "copy number" is defined herein as the number of molecules, per genome, of a gene which is contained in a cell. Methods for determining the copy number of a gene are will known in the art and include Southern analysis, quantitative PCR, or real time PCR.

The fungal host cell preferably contains at least two copies, more preferably at least four copies, even more preferably at least six copies, most preferably at least eight copies, and even most preferably at least ten copies of the first nucleic acid sequence encoding a polypeptide of interest.

Polypeptide Encoding Nucleic Acid Sequences

The polypeptide encoded by the first nucleic acid sequence may be native or heterologous to the fungal host cell of interest.

The term "polypeptide" is not meant herein to refer to a specific length of the encoded product and, therefore, encompasses peptides, oligopeptides, and proteins. The term "heterologous polypeptide" is defined herein as a polypeptide which is not native to the fungal cell, a native polypeptide in which modifications have been made to alter the native sequence, or a native polypeptide whose expression is quantitatively altered as a result of a manipulation of the fungal cell by recombinant DNA techniques.

Preferably, the polypeptide is a hormone or variant thereof, enzyme, receptor or portion thereof, antibody or portion thereof, or reporter. In a preferred embodiment, the polypeptide is secreted extracellularly. In a more preferred embodiment, the polypeptide is an oxidoreductase, transferase, hydrolase, lyase, isomerase, or ligase. In an even more preferred embodiment, the polypeptide is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, or xylanase.

The nucleic acid sequence encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a nucleic acid sequence encoding a polypeptide of interest are known in the art and include isolation from genomic DNA, preparation from cDNA, or a combination thereof. The cloning of the nucleic acid sequence from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the mutant fungal cell where multiple copies or clones of the nucleic acid sequence will be replicated. The nucleic acid sequence may be of genomic, cDNA, RNA, semisynthetic, synthetic origin, or any combinations thereof.

In the methods of the present invention, the polypeptide may also include a fused or hybrid polypeptide in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptide may comprise a combination of partial or complete polypeptide sequences obtained from at least two different polypeptides wherein one or more may be heterologous to the mutant fungal cell.

Nucleic Acid Constructs

The present invention also relates to nucleic acid constructs comprising a first nucleic acid sequence encoding the polypeptide in tandem with a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, wherein the crippled translational initiator sequence comprises a T at the −3 position and a T at one or more of the −1, −2, and −4 positions. The nucleic acid sequences are operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated nucleic acid sequence encoding a polypeptide may be further manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

In the methods of the present invention, the nucleic acid sequences may comprise one or more native control sequences or one or more of the native control sequences may be replaced with one or more control sequences foreign to the nucleic acid sequence for improving expression of the coding sequence in a host cell.

The term "control sequences" is defined herein to include all components which are necessary or advantageous for the expression of a polypeptide of interest. Each control sequence may be native or foreign to the nucleic acid sequence encoding the polypeptide. Such control sequences include, but are not limited to, a leader, polyadenylation sequence, propeptide sequence, crippled translational initiator sequence of the present invention, signal peptide sequence, and transcription terminator. At a minimum, the control sequences include a crippled translational initiator sequence of the present invention, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

Expression Vectors

The present invention also relates to recombinant expression vectors comprising a crippled translational initiator sequence operably linked to a gene encoding a selectable marker in which the 3' end of the crippled translational initiator sequence is immediately upstream of the initiator codon of the gene encoding the selectable marker and a nucleic acid sequence encoding a polypeptide of interest as well as any control sequences involved in the expression of the sequences, wherein the crippled translational initiator sequence comprises a T at the −3 position and a T at one or more of the −1, −2, and −4 positions. The various nucleic acid and control sequences described above may be joined together to produce a recombinant expression vector which may include one or more convenient restriction sites to allow for insertion or substitution of the promoter and/or nucleic acid sequence encoding the polypeptide at such sites.

Alternatively, the nucleic acid sequence may be expressed by inserting the nucleic acid sequence or a nucleic acid construct comprising the crippled translational initiator sequence and/or sequence into an appropriate vector for expression. In creating the expression vector, the coding sequence is located in the vector so that the coding sequence is operably linked with a crippled translational initiator sequence of the present invention and one or more appropriate control sequences for expression.

The recombinant expression vector may be any vector (e.g., a plasmid or virus) which can be conveniently subjected to recombinant DNA procedures and can bring about the expression of a nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention also contain one or more selectable markers which permit easy selection of transformed cells as described earlier.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

The procedures used to ligate the elements described above to construct the recombinant expression vectors of the present invention are well known to one skilled in the art (see, e.g., Sambrook et al., 1989, supra).

Host Cells

The present invention also relates to methods for obtaining a fungal host cell for production of a polypeptide, comprising: (a) integrating into the genome of the fungal cell a nucleic acid construct comprising a first nucleic acid sequence encoding the polypeptide in tandem with a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, wherein the crippled translational initiator sequence comprises a T at the −3 position and a T at one or more of the −1, −2, and −4 positions; and (b) isolating the fungal host cell under conditions that select for multiple copies of the selectable marker wherein the copy number of the first nucleic acid sequence is increased.

The term "genome" is defined herein as the complete set of DNA of a cell including chromosomal, artificial chromosomal DNA, and extrachromosomal DNA, i.e., self-replicative genetic elements.

The present invention also relates to recombinant host cells comprising a first nucleic acid sequence encoding a polypeptide in tandem with a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, wherein the crippled translational initiator sequence comprises a T at the −3 position and a T at one or more of the −1, −2, and −4 positions, which host cells are advantageously used in the recombinant production of the polypeptide. A construct or vector comprising such sequences is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any fungal cell useful in the methods of the present invention. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In a more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae,*

*Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

In an even most preferred embodiment, the Fusarium venenatum cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, Gene 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75:1920.

The present invention is further described by the following examples which should not be construed as limiting the scope of the invention.

EXAMPLES

Chemicals used as buffers and substrates were commercial products of at least reagent grade. Primers were synthesized with an Applied Biosystems Model 394 DNA/RNA Synthesizer (Applied Biosystems, Inc., Foster City, Calif.) according to the manufacturer's instructions.

Media and Solutions

MY25 medium at pH 6.5 was composed per liter of 25 g of maltose, 2.0 g of $MgSO_4.7H_2O$, 10 g of $KH_2PO_4$, 2.0 g of citric acid, 10 g of yeast extract, 2.0 g f $K_2SO_4$, 2.0 g of urea, 1.0 ml of $CaCl_2.2H_2O$ (100 g/l stock solution), and 0.5 ml of trace metals solution. MY25 microtiter medium was diluted 1:100 with 490 ml glass distilled water and 500 ml 2× MY Salts. Cultures were grown at 34° C.

2× MY Salts pH 6.5 solution was composed per liter of 4 g of $MgSO_4.7H_2O$, 4 g of $K_2SO_4$, 20 g of $KH_2PO_4$, 4 g of citric acid, 1 ml of trace metals solution, and 2 ml of $CaCl_2.2H_2O$ (100 g/l stock solution).

Minimal medium was composed per liter of 6 g of $NaNO_3$, 0.52 g of KCl, 1.52 g of $KH_2PO_4$, 1 ml of trace metals, 10 g of glucose, 500 mg of $MgSO_4.7H_2O$, 342.3 g of sucrose, and 20 g of Noble agar at pH 6.5. Transfer plates were the same as above, but omitting the sucrose.

MLC medium pH 5.0 is composed per liter of tap water of 40 g of glucose, 50 g of soy bean powder, 4g of citric acid, 1 ml of pluronic acid.

MU-1 medium pH 4.5 was composed per liter 260 g of Malt dextrin, 3 g of $MgSO_4.7H_2O$, 6 g of $K_2SO_4$, 5 g of $KH_2PO_4$, 0.5 ml of COVE trace metal solution, 1 ml of pluronic acid.

COVE plates were composed per liter of 343.3 g of sucrose, 20 ml of COVE salts solution, 10 ml of 1 M acetamide, 10 ml of 3 M CsCl, and 25 g of Nobel agar. The COVE salts (50×) solution was comprised of 26 g of KCl, 26 g of $MgSO_{4-7}H_2O$, 76 g of $KH_2PO_4$, and 50 ml of COVE trace metals solution. COVE trace metals solution was composed of (per liter): 0.04 g of $NaB_4O_7-10H_2O$, 0.040 g of $CuSO_4-5H_2O$, 0.70 g of $FeSO_4-H_2O$, 0.80 g of $Na_2MoO_2-2H_2O$, and 10 g of $ZnSO_4$.

Minimal medium 5FOA was composed per liter of 6 g of $NaNO_3$, 0.52 g of KCl, 1.52 g of $KH_2PO_4$, 1 ml of COVE trace elements, 2.44 g of uridine, 20 g of Noble agar, 1 g of 5-fluoroorotic acid, 20 ml of 50% glucose, and 2.5 ml of 20% $MgSO_4.7H_2O$.

The trace metals solution (1000×) was composed per liter of 22 g of $ZnSO_4.7H_2O$, 11 g of $H_3BO_3$, 5 g of $MnCl_2.4H_2O$, 5 g of $FeSO_4.7H_2O$, 1.6 g of $CoCl_2.5H_2O$, 1.6 g of $(NH_4)_6Mo_7O_{24}$, and 50 g of $Na_4EDTA$.

YEG medium was composed per liter of 5 g yeast extract and 20 g dextrose.

Working dilution of TM buffer pH 7.2 was composed per liter of 2.6 g of Tris and 1 g of maleic acid. A 5× stock of TM buffer was made and stored.

Agarose plates for the rocket immunoelectrophoresis were 1 g of agarose (Bio-Rad) in 100 ml of TM buffer.

Destaining solution for RIE was made by mixing 450 ml of ethanol, 100 ml of acetic acid, and 450 ml of deionized water.

Staining solution for RIE was made by mixing 1000 ml of destaining solution with 5 g of Coomassie brilliant blue.

Example 1
Construction of pBANe10 pBANe10 was constructed as described below to contain the TAKA/NA2-tpi leader hybrid promoter, the lipase gene from *Humicola lanuginosa* bordered by a PacI and SwaI site, the AMG terminator, and the full-length *Aspergillus nidulans* pyrG gene as a selectable marker.

PCR was employed to insert an EcoRI site at the 5' end and a SwaI site at the 3' end of the NA2-tpi leader hybrid promoter of pJaL292 (FIG. 1) using primers 1 and 2 below.
Primer 1: 5'-TGGTGTACAGGGGCATAAAAT-3' (SEQ ID NO. 1)
Primer 2: 5'-ATTTAAATCCAGTTGTGTATATAGAGGATTG TGG-3' (SEQ ID NO. 2) Amplification reactions (100 µl) were prepared using approximately 0.2 µg of pJaL292 as the template. Each reaction contained the following components: 0.2 µg of plasmid DNA, 48.4 pmol of the forward primer, 48.4 pmol of the reverse primer, 1 mM each of dATP, dCTP, dGTP, and dTTP, 1× Taq DNA polymerase buffer, and 2.5 U of Taq DNA polymerase (Perkin-Elmer Corp., Branchburg, N.J.). The reactions were incubated in an Ericomp TwinBlock™ System (Ericomp, Inc., San Diego, Calif.) programmed as follows: One cycle at 95° C. for 5 minutes followed by 30 cycles each at 95° C. for 1 minute, 55° C. for 1 minute and 72° C. for 2 minutes.

The PCR products were electrophoresed on a 1% agarose gel to confirm the presence of a 0.6 kb NA2-tpi fragment.

Figure 2:
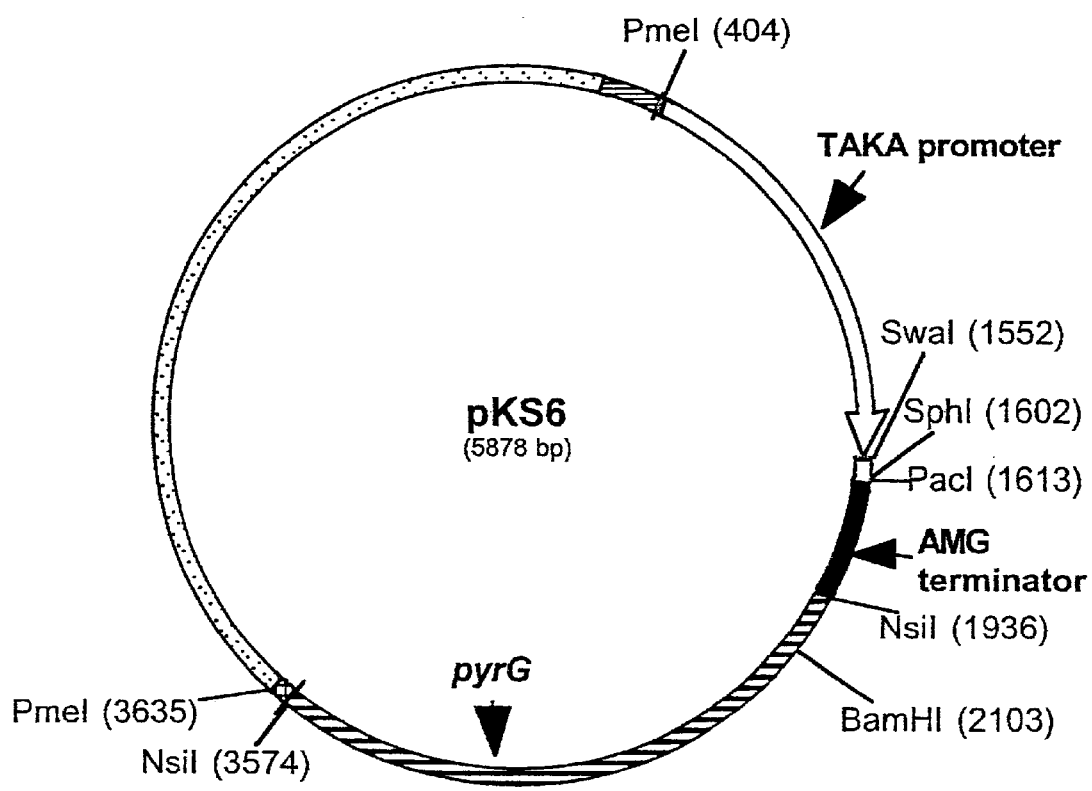
FIG. 2 shows a restriction map of pKS6.
Figure 3:
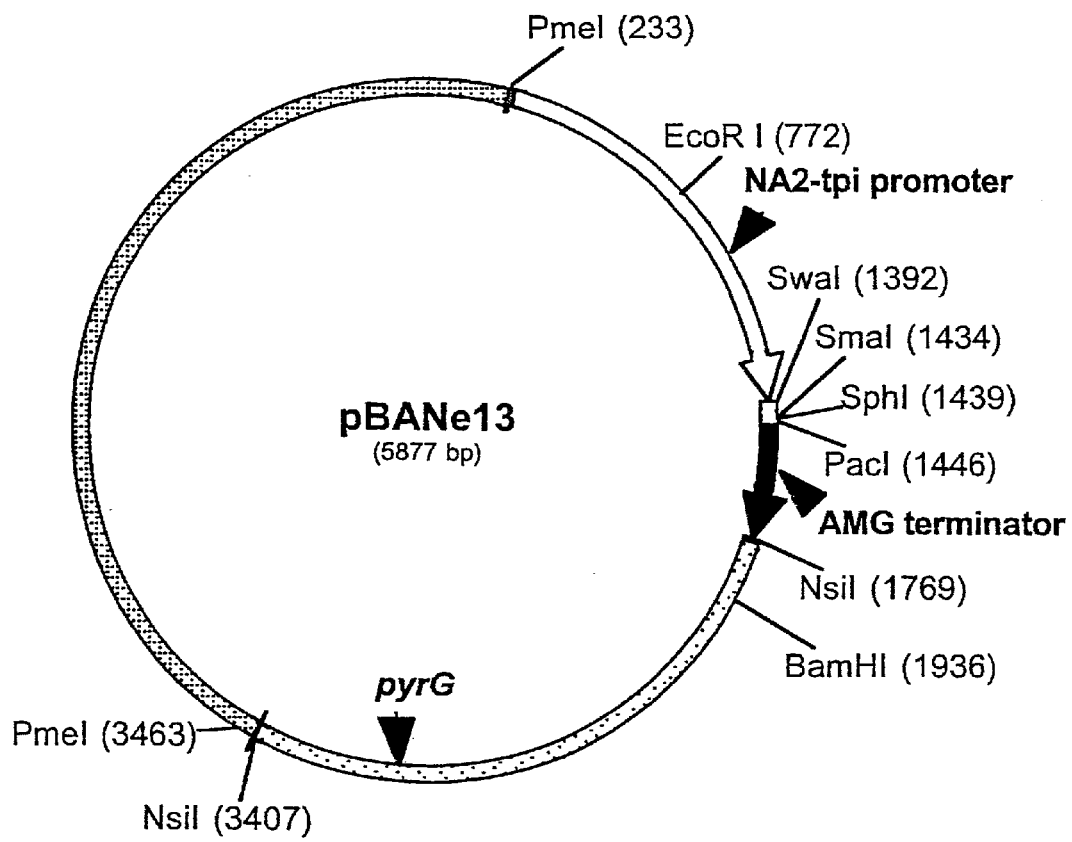
FIG. 3 shows a restriction map of pBANe13.

The PCR product was subsequently subcloned into pCRII using a TA Cloning Kit (Invitrogen, Carlsbad, Calif.) according to the manufacturer's instructions. The transformants were then screened by extracting plasmid DNA from the transformants using a QIAwell-8 Plasmid Kit (Qiagen, Inc., Chatsworth, Calif.) according to the manufacturer's instructions, and restriction digesting the plasmid DNA with EcoRI/SwaI followed by agarose electrophoresis to confirm the presence of the 0.6 kb fragment, for the SwaI/EcoRI NA2-tpi fragment. In order to confirm the PCR products, the products were sequenced with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38: 47–60) using the M13 reverse (−48) and M13 forward (−20) primers (New England Biolabs, Beverly, Mass.) and primers unique to the DNA being sequenced. The plasmids from the correct transformants were then digested with the restriction enzymes for which the plasmids were designed, separated on a 1% agarose gel, and purified using a FMC SpinBind Kit (FMC, Rockland, Me.) according to the manufacturer's instructions.

pKS6 (FIG. 2), which contains the TAKA amylase promoter, a polylinker, the AMG terminator, and the *Aspergillus nidulans* pyrG gene, was digested with EcoRI and SwaI to remove a portion of the TAKA amylase promoter. This region was replaced with the NA2-tpi PCR product to produce pBANe13 (FIG. 3).

The oligonucleotide primers 3 and 4 shown below were used to insert restriction sites flanking the lipase gene by PCR amplification:
Primer 3: 5'-ATTTAAATGATGAGGAGCTCCCTTGTGCTG-3' (SEQ ID NO. 3)
Primer 4: 5'-TTAATTAACTAGAGTCGACCCAGCCGCGC-3' (SEQ ID NO. 4)

Figure 4:
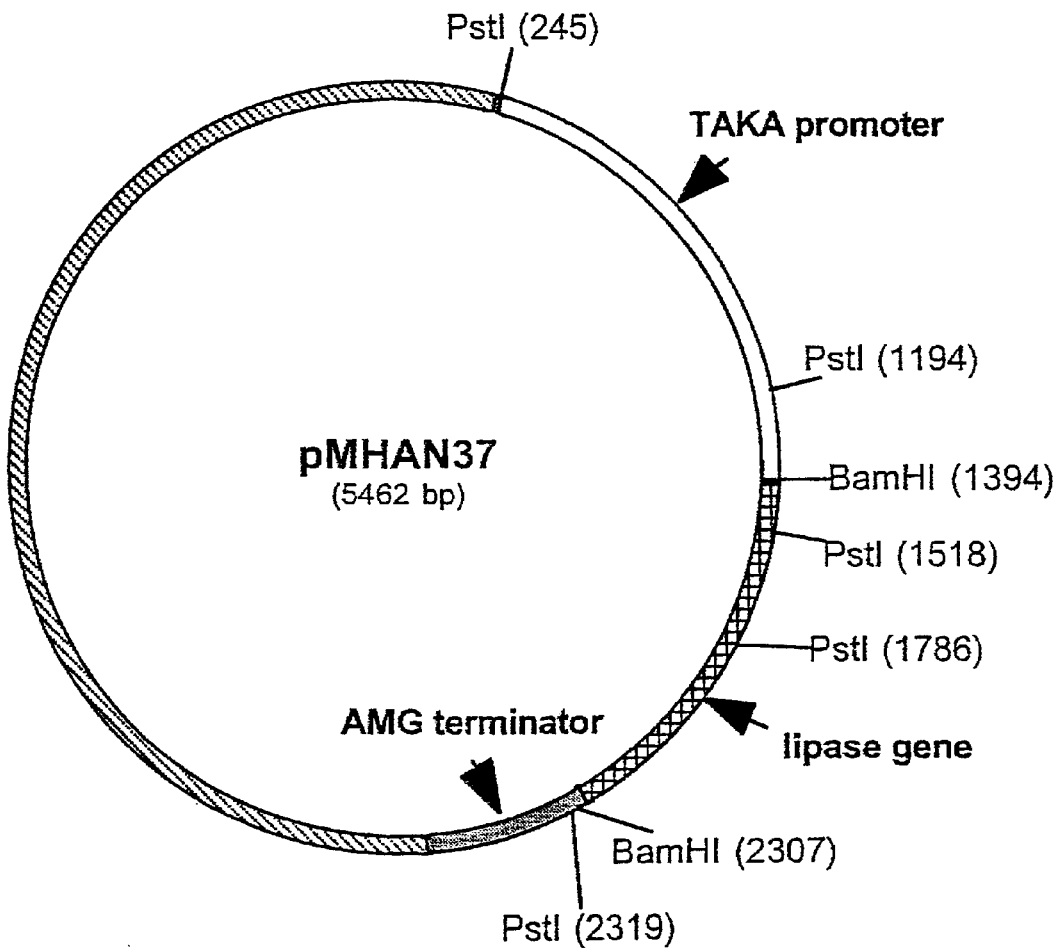
FIG. 4 shows a restriction map of pMHan37.

The amplification reaction (100 µl) was prepared using approximately 0.2 µg of pMHan37 (FIG. 4) as a template with primers 3 and 4. The reaction contains the following components: 0.2 µg pMHan37, 48.4 pmol primer 3, 48.4 pmol primer 4, 1 mM each dNTP, 1 × Taq polymerase buffer, and 2.5 U Taq polymerase. The reaction was incubated in an Ericomp Thermal Cycler programmed as follows: One cycle at 95° C. for 5 minutes followed by 30 cycles at 95° C. for 1 minute, 55° C. for 1 minute and 72° C. for 2 minutes. Two µl of the reaction was electrophoresed on an agarose gel to confirm the amplification of the lipase product of approximately 900 bp.

The PCR amplified lipase gene was subcloned into pCRII using the TA Cloning Kit according to the manufacturer's instructions. The transformants are then screened by extracting plasmid DNA from the transformants using a QIAwell-8 Plasmid Kit according to the manufacturer's instructions, restriction digesting the plasmid DNA with SwaI/PacI, and sequencing the DNA using an Applied Biosystems Automatic DNA Sequencer Model 377, Version 3.0 (Applied Biosystems, Inc., Foster City, Calif.). according to the manufacturer's instructions to confirm the PCR product.

The lipase gene was excised from the pCRII plasmid by digesting with SwaI and PacI and was subsequently subcloned into pBANe13 digested with SwaI/PacI to yield pBANe10.

Example 2
Construction of pBANe10 Variants

The nucleotide sequence upstream of the *Aspergillus nidulans* pyrG gene in pBANe10 is ACCGCCATCATGT with the minus 3 position containing an A nucleotide. The nucleotide sequence upstream of the Aspergillus nidulans pyrG gene was changed using a Stratagene QuikChange™ Site-Directed Mutagenesis Kit (Stratagene Cloning Systems, La Jolla, Calif.) following the manufacturers instructions and using the primers listed below, producing 5 variants of pBANe10.

```
Primer 5:   5'-CATTGGAGAACCGCCGTCATGTCTTCGAAGTCC-3'  (SEQ ID NO.5)

Primer 6:   5'-GGACTTCGAAGACATGACGGCGGTTCTCCAATG-3'  (SEQ ID NO.6)

Primer 7:   5'-CATTGGAGAACCGCCCTCATGTCTTCGAAGTCC-3'  (SEQ ID NO.7)

Primer 8:   5'-GGACTTCGAAGACATGAGGGCGGTTCTCCAATG-3'  (SEQ ID NO.8)

Primer 9:   5'-CATTGGAGAACCGCCTTCATGTCTTCGAAGTCC-3'  (SEQ ID NO.9)

Primer 10:  5'-GGACTTCGAAGACATGAAGGCGGTTCTCCAATG-3'  (SEQ ID NO.10)
```

-continued

Primer 11:  5'-CATTGGAGAACCGGTTTTATGTCTTCGAAGTCC-3' (SEQ ID NO.11)

Primer 12:  5'-GGACTTCGAAGACATAAAACCGGTTCTCCAATG-3' (SEQ ID NO.12)

Primers 5 and 6 were used to construct pBANe10G, primers 7 and 8 were used to construct pBANe10C, and primers 9 and 10 were used to construct pBANe10T. These plasmids differ from pBANe10 only at the minus 3 position with pBANe10G containing a G nucleotide, pBANe10C containing a C nucleotide, and pBANe10T containing a T nucleotide at the minus 3 position. Primers 11 and 12 were used to construct pBANe10-1-4 which differs from pBANe10 at the positions minus 5 to minus 1. pBANe10 contains the nucleotides CCATC in positions minus 5 to minus 1. These were changed to GTTTT producing pBANe10-1-4.

The PCR reactions were incubated in a Perkin Elmer 9600 GeneAmp PCR System (Norwalk, Conn.) programmed for one cycle at 95° C. for 30 seconds followed by 12 cycles each at 95° C. for 30 seconds, 55° C. for 1 minute and 68° C. for 14 minutes. The PCR reactions were treated with 10 units of DpnI to digest the non-mutated parental DNA. The digest reactions were then used to transform *E. coli* XL1-Blue supercompetent cells following the Stratagene QuikChange™ Site-Directed Mutagenesis Kit protocol. The nucleotide sequence of pBANe10-1-4 was determined using TAQ polymerase cycle-sequencing with fluorescent labeled nucleotides. The sequencing reactions were electrophoresed on an Applied Biosystems Automatic DNA Sequencer Model 377, Version 3.0 according to the manufacturer's instructions. The following primers were used for sequencing.

Sequencing primer 971227: 5'-AATGATAGTCGGGTTCGTGAC-3' (SEQ ID NO. 13)

Sequencing primer 971228: 5'-TATCCTGGAGGGGCATTGGTG-3' (SEQ ID NO. 14)

Example 3

Construction of JaL250

Figure 5:
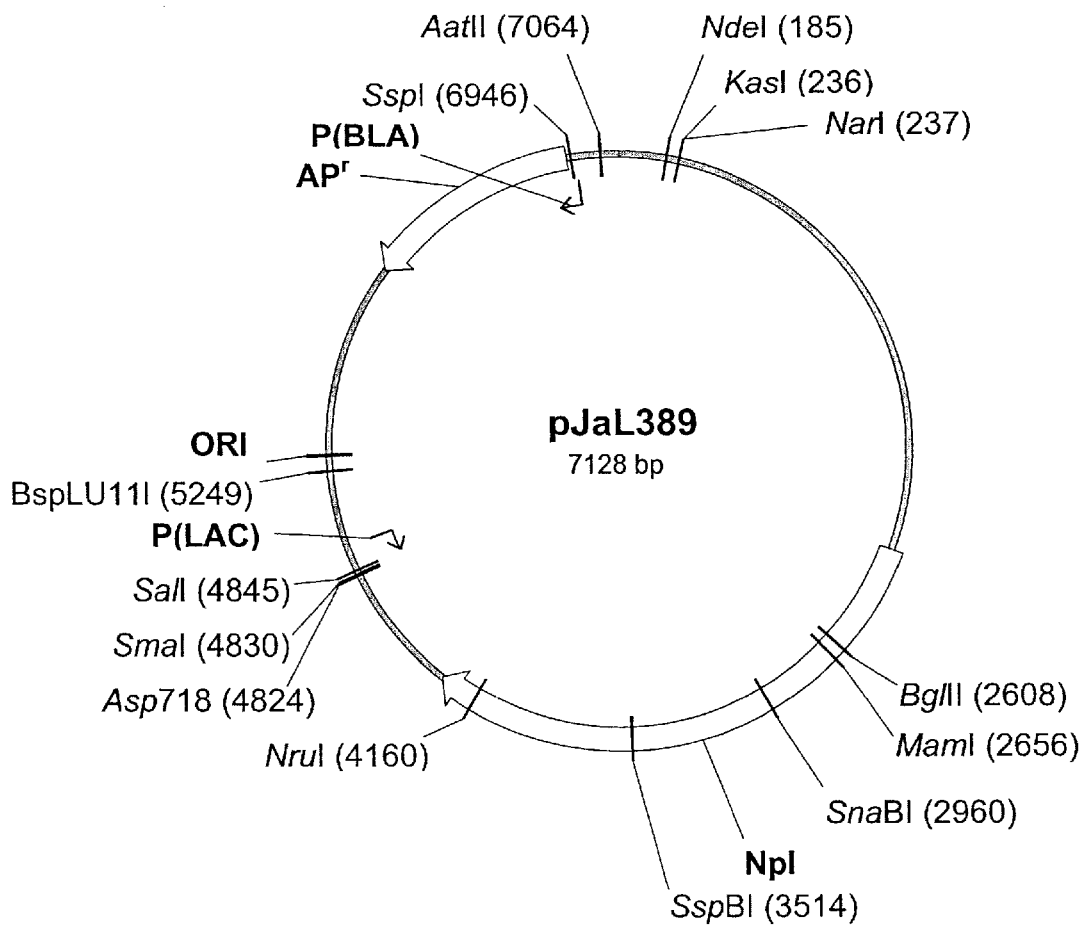
FIG. 5 shows a restriction map of pJaL389.
Figure 6:
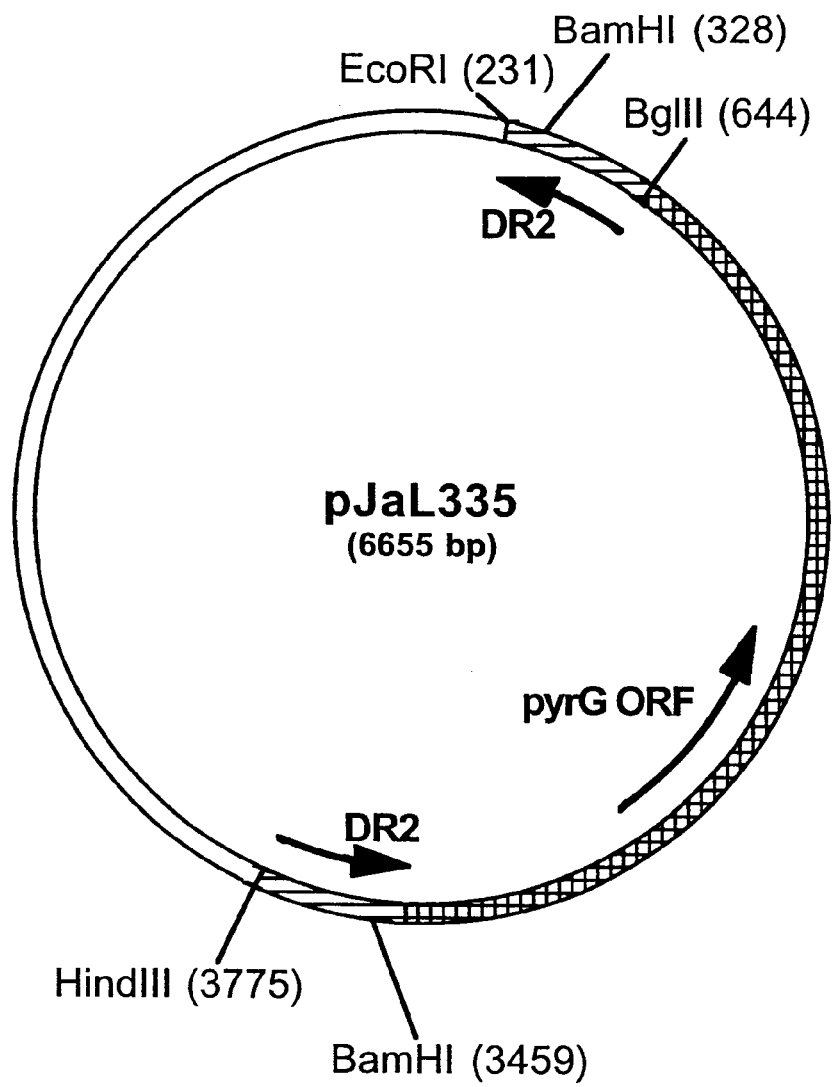
FIG. 6 shows a restriction map of pJaL335.
Figure 7:
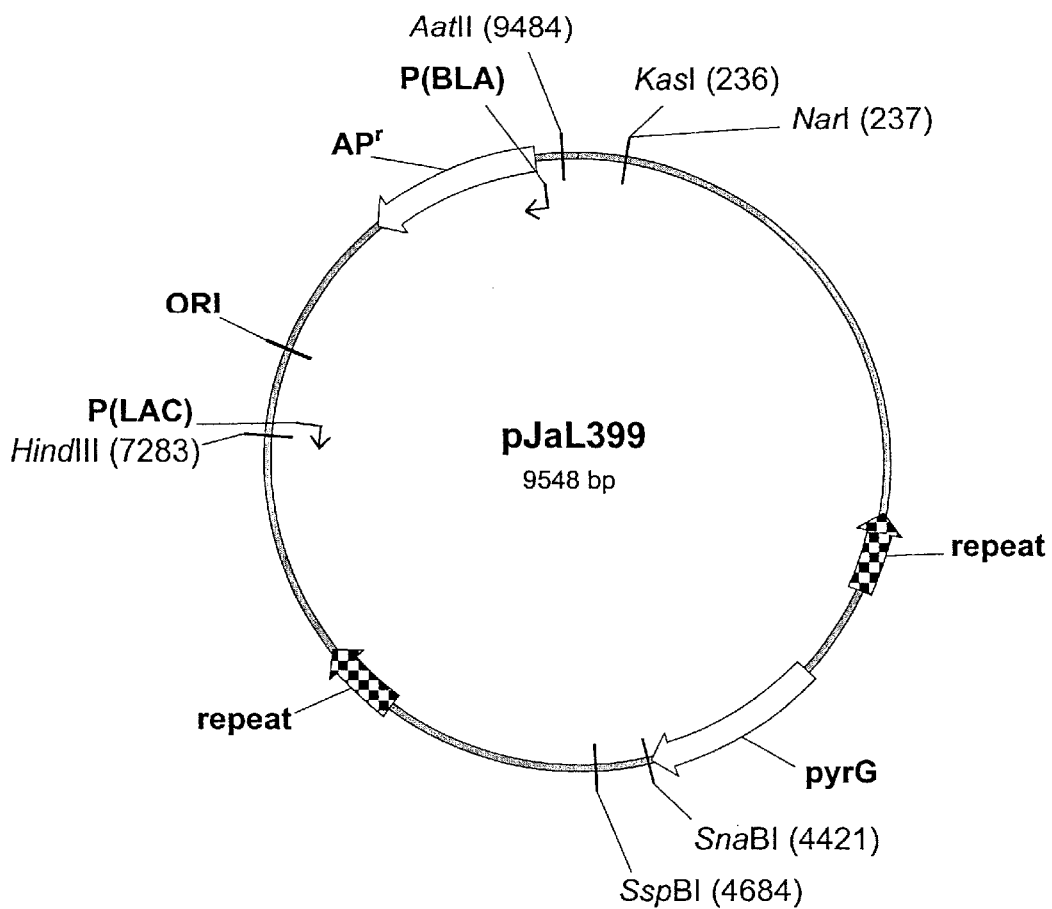
FIG. 7 shows a restriction map of pJaL399.

*Aspergillus oryzae* JaL250 was constructed from *Aspergillus oryzae* JaL142 (Christensen et al., 1988, Bio/Technology 6: 1419–1422) by deleting the neutral protease I gene (npI). The npI deletion plasmid was constructed by exchanging a 1.1 kb BalI fragment coding for the central part of the npI gene in plasmid pJaL389 (FIG. 5), which contained a 5.5 kb SacI genomic fragment encoding the npI gene, with a 3.5 kb HindIII fragment from pJaL335 (FIG. 6) containing the pyrG gene flanked by repeat sequences, thereby creating plasmid pJaL399 (FIG. 7). *Aspergillus oryzae* JaL142 was transformed with the 7.9 kb SacI fragment. Transformants were selected by relief of the uridine requirement on Minimal medium plates. The transformants were analyzed by Southern analysis and by IEF protease profile analysis according to standard methods.

Two out of 35 transformants possessed an altered Southern profile compared to the parent strain and displayed no neutral protease I activity by IEF. Furthermore, Southern analysis showed that one of the two transformants had a clean deletion of the npI gene and was designated *Aspergillus oryzae* JaL228.

Totally, 2.3×10$^7$ conidiospores of *Aspergillus oryzae* JaL228 were spread on Minimal medium plates supplemented with 0.1% 5-fluoro-orotic acid (FOA) and 10 mM uridine. Eight FOA resistant colonies were obtained. A Southern blot of BamHI digested genomic DNA from the eight colonies probed with a 401 bp pyrG repeated region demonstrated that the pyrG gene had been excised by recombination at the repeated regions. *Aspergillus oryzae* JaL228 showed two bands of the expected size of 2.7 and 3.1 kb originating from the two copies of the repeated region. If the pyrG gene had been lost by recombination between the repeated regions, the 3.1 kb band would have disappeared and only the 2.7 kb would have remained. All 8 FOA resistant colonies showed this pattern of bands. Sequencing of a PCR fragment covering the junctions between the npI gene and the copy of the 401 bp repeat remaining in the 8 colonies confirmed that the pyrG gene was excised by recombination between the repeat sequences. One of the colonies was designated *Aspergillus oryzae* JaL250.

Example 4

Transformation of *Aspergillus oryzae* JaL250

*Aspergillus oryzae* JaL250 was grown in 100 ml of YEG at 34° C. for 16–18 hours with agitation at 160 rpm. The mycelia were recovered by filtration through a 0.45 μm filter until approximately 10 ml remained on the filter, washed with approximately 20 ml of 1 M MgSO$_4$.7H$_2$O (0.45 μm filtered), and then collected with a sterile loop and placed in a 125 ml Ehrlenmeyer flask. The mycelia were then resuspended in 75 mg of NOVOZYM 234™ (Novo Nordisk A/S, Bagsvaerd, Denmark) in 15 ml of 1 M MgSO$_4$.7H$_2$O. The suspension was incubated at 37° C. with gentle agitation at 50 rpm for approximately one hour to generate protoplasts.

The contents of the 125 ml Ehrlenmeyer flask were then filtered through sterile Miracloth into a 30 ml Corex centrifuge tube, overlaid with 6 ml of 0.6 M sorbitol-100 mM Tris pH 7.0, and centrifuged at 3500 × g for 15 minutes in a swinging bucket rotor to recover the protoplasts. The protoplasts were recovered from the buffer interface with a Pasteur pipet. The protoplasts were then washed with two volumes of 1.2 M sorbitol-10 mM Tris-10 mM CaCl$_2$.2H$_2$O pH 7.5 (STC) and centrifuged at 3500 × g for 5 minutes. The protoplasts were rewashed in 10 ml of STC and centrifuged as before two times. The protoplasts were resuspended in STC to a final concentration of 1.7×10$^7$ protoplasts per ml.

Transformation of *Aspergillus oryzae* JaL250 for pyrG selection was conducted with protoplasts at a concentration of 1.7×10$^7$ protoplasts per ml. Ten μg of DNA (pBANe10, pBANe10G, pBANe10C., pBANe10T, and pBANe10-1-4T) were added to 100 μl of protoplasts. A volume of 250 μl of PEG solution (60% PEG 4000-10 mM CaCl$_2$) was then added and the mixture was placed at 37° C. for 30 minutes. Four ml of STC were then added and the mixture was plated onto Minimal medium plates selecting for pyrG. The plates were incubated 5–7 days at 37° C. The transformants were purified by streaking spores and picking isolated colonies from Minimal medium plates.

The *Aspergillus oryzae* JaL250 transformants were checked by PCR for the presence of the lipase gene. The following primers were used in the PCR reactions:
Primer 13: 5'-CCGGAATGTTAGGCTGGTT-3' (SEQ ID NO. 15)
Primer 14: 5'-TTCTTTGTCTCTGCGTGGAC-3' (SEQ ID NO. 16)

Amplification reactions (100 µl) were prepared using approximately 2 µg of DNA from the appropriate transformant as the template. Each reaction contained the following components: 2 µg of DNA, 50 pmol of primer 13, 50 pmol of primer 14, 25 mM each of dATP, dCTP, dGTP, and dTTP, 1× Taq DNA polymerase buffer, and 5 U of Taq DNA polymerase (Perkin-Elmer Corp., Branchburg, N.J.). The reactions were incubated in an Ericomp TwinBlock™ System programmed as follows: One cycle at 95° C. for 3 minutes followed by 30 cycles each at 95° C. for 1 minute, 60° C. for 1 minute and 72° C. for 2 minutes, followed by 1 cycle at 72° C. for 2 minutes.

The PCR products were electrophoresed on a 1% agarose gel using 1× 45 mM Tris-borate-1 mM EDTA to confirm the presence of lipase gene.

Example 5

Analysis of Transformants for Lipase Production

The *Aspergillus oryzae* JaL250 transformants containing the lipase gene were assayed for lipase expression. For microtiter assays, MY25 medium was diluted 100 fold with 49% glass distilled $H_2O$ and 50% 2× MY Salts pH 6.5 solution. 1.25 ml of 1/100 strength MY25 medium was added to the wells of a 24 well cell culture plate. The wells were inoculated with 10 µl of spores from each transformant, and the plates were incubated at 34° C. with agitation at 100 rpm. Each transformant was inoculated into three wells. Untransformed *Aspergillus oryzae* JaL250 was used to inoculate three wells. Samples were taken from the 24 well cell culture plates on day 3 and day 5.

On day 3 and day 5, 100 µl of broth was removed from each well. Each sample was diluted with 200 µl of 100 mM AOS/MOPS pH 7.5 and placed into a 96 well microtiter plate to be assayed for lipase activity.

Samples of 100 µl were removed on days 3 and 5 from each well of the 24 well cell culture plates. Each sample was diluted with 200 µl of 100 mM alpha olefin sulfonate (AOS) detergent in 4 mM $CaCl_2$-100 mM MOPS pH 7.5 (MC buffer) and 20 µl aliquots were dispensed to wells in 96-well plates followed by 200 µl of diluted substrate. The lipase assay substrate was prepared by diluting 1:50 a p-nitrophenylbutyrate stock substrate (21 µl of p-nitrophenylbutyrate/ml DMSO) into MC buffer immediately before use. Standard lipase (LIPOLASE™, Novo Nordisk A/S, Bagsvaerd, Denmark) was prepared to contain 40 LU/ml of MC buffer containing 0.02% AOS detergent. The standard was stored at 4° C. until use. Standard lipase was diluted 1/40 in MC buffer just before use. Using a plate reader, the absorbance at 405 mn was recorded as the difference of two readings taken at approximately 1 minute intervals. Lipase units/ml (LU/ml) were calculated relative to the lipase standard. The results of the lipase assays are shown in Table 1 relative to lipase activity obtained with pBANe10 normalized to 1.0.

TABLE 1

Lipase Expression by *Aspergillus oryzae* JaL250 transformants

| Plasmid DNA | # Transformants screened | Mean lipase expression (LU/ml) | Median lipase expression (LU/ml) |
|---|---|---|---|
| pBANe10 | 40 | 1.0 | 1.0 |
| pBANe10G | 39 | 0.90 | 1.07 |
| pBANe10C | 39 | 1.21 | 1.07 |
| pBANe10T | 41 | 1.10 | 1.04 |
| pBANe10-1-4 | 37 | 1.81 | 2.74 |

As shown in Table I, there was no significant change in expression of the *Humicola lanuginosa* lipase gene when the nucleotide at the minus 3 position of the selectable marker (*Aspergillus nidulans* pyrG gene) was changed from the wild type translational initiator sequence (pBANe10) to a non-consensus translational initiator sequence (pBANe10G, pBANe10C, and pBANe10T). When the nucleotides upstream of the *Aspergillus nidulans* pyrG gene were further changed to a more crippled translational initiator (pBANe10-1-4), there was a significant increase in expression of the *Humicola lanuginosa* lipase gene.

Example 6

Copy Number Analysis

Lipase copy number in the *Aspergillus oryzae* mutants was determined by real time PCR analysis using an Applied Biosystems Prism Model 7700 Sequence Detector (Applied Biosystems, Inc., Foster City, Calif.) according to the manufacturer's instructions. Real time PCR reactions were performed on each genomic DNA preparation for both lipase and a single copy gene control oliC. Spores of the mutants were grown in 5 ml of YEG medium for 24 hours at 34° C. in a small Petri plate. Mycelia were then collected from each culture by filtration through Whatman filter paper No. 1 (Whatman, Springfield Mill, England) and transferred to a 1.7 ml centrifuge tube. The mycelial preparations were frozen in liquid nitrogen and dried in a SpeedVac (Savant Instruments, Inc., Farmingdale, N.Y.) for 1.5 hours at room temperature. Genomic DNA was obtained using the DNeasy Kit (Qiagen, Chatsworth, Calif.) according to the manufacturer's instructions. The average lipase copy number for each strain was calculated by taking a ratio of lipase amplicon quantity to oliC amplicon quantity. Standard curves for the analysis were generated using genomic DNA from *Aspergillus oryzae* HowB430. The following primers and probe were used for real time amplification of the lipase gene:

```
Lipase gene probe:                          6FAM-5'-TGGCCAGTCCTATTCGTCGAGAGGTC-3'-TAMRA   (SEQ ID NO. 17)

Lipase gene forward primer (lipo9F):        5'-CTCCCTTGTGCTGTTCTTTGTCT-3'                 (SEQ ID NO. 18)

Lipase gene reverse primer (lipo111R):      5'-CTGTGCAAAGAGATTGAACTGGTTA-3'               (SEQ ID NO. 19)
```

The following primers and probe were used for real time amplification of oliC:

| | | |
|---|---|---|
| oliC probe: | 6FAM-5'-TGGGTATGGGTTCCGCCGCC-3'-TAMRA | (SEQ ID NO. 20) |
| oliC forward primer (oliC4F): | 5'-GATGGTCCAGGTCTCCCAGAA-3' | (SEQ ID NO. 21) |
| oliC reverse primer (oliC122R): | 5'-CAGGGTTGCGGGAGACA-3' | (SEQ ID NO. 22) |

6FAM is an abbreviation for the fluorescent reporter 6-carboxyfluorescein which is covalently linked to the 5' end of the probes, and TAMRA is an abbreviation for 6-carboxytetramethylrhodamine, which is a quencher attached via a linker arm to the 3' end of the probe.

For the standard curve, Aspergillus oryzae HowB430 genomic DNA was serially diluted 1:10, 1:100, 1:1000 and 1:10000, and real time PCRs were run for both primers/probe sets. For analysis of other strains, genomic DNA was diluted either 1:50 and 1:100 or 1:100 and 1:200, and real time amplifications were run with both primers/probe sets. The real time amplification reactions were set up using TaqMan PCR Reagent kits (Applied Biosystems, Inc., Foster City, Calif.) according to the manufacturer's instructions. The reactions contained 1× TaqMan Buffer A, 3.5 mM $MgCl_2$, 200 µM each of dATP, dCTP, dGTP and dUTP, 0.025 U/ml AmpliTaq Gold, 0.01 U/ml AmpErase, and either the lipase gene or oliC probes at 100 µM. Lipase primers were added at a final concentration of 0.9 µM each. The oliC primers were added at a final concentration of 0.3 µM. The reactions were run using the following cycling conditions on the Applied Biosystems Prism Model 7700 Sequence Detector: 1 cycle at 50° C. for 2 minutes, 1 cycle at 95° C. for 10 minutes, and 40 cycles each at 95° C. for 15 seconds and 60° C. for 1 minute. The raw data was analyzed using the Sequence Detector v 1.6.

The results obtained are shown in Table 2 below where the average lipase gene copy number of Aspergillus oryzae JaL250/BANe10 was normalized to 1.0. As shown in Table 2, the copy number of the Humicola lanuginosa lipase gene increased, similar to the expression of lipase, when the nucleotides upstream of the selectable marker (Aspergillus nidulans pyrG gene) were changed from the wild type sequence (pBANe10) to a crippled translational initiator sequence (pBANe10-1-4).

TABLE 2

Copy number of lipase in Aspergillus oryzae JaL250 transformants

| Plasmid DNA | # transformants screened | Mean copy # lipase | Median copy # lipase |
|---|---|---|---|
| pBANe10 | 40 | 1.0 | 1.0 |
| pBANe10-1-4 | 37 | 1.51 | 3.71 |

Example 7
Construction of the Host Strain Aspergillus niger 303-10

The host strain Aspergillus niger 303-10 was isolated spontaneously on minimal medium 5FOA agar plates. Aspergillus niger JaL303 was constructed by site-directed gene disruption to interrupt the resident tripeptidyl aminopeptidase (TPAP) gene in Aspergillus niger 1-3-2.

Aspergillus niger 70-56 was constructed as follows. Lyophilized conidia of the strain Aspergillus niger Bo95 were irradiated with γ-ray at the strength of 125 Krad or 150 Krad to cause random mutations to the cell. The resulting conidia were re-hydrated with liquid medium and inoculated to microtiter plates containing suitable medium with no more than one conidium per well to screen for amyloglucoamylase yield improved mutants using a robotics system. Amyloglucoamylase activity was determined in microtiterwells where 25 µl of each sample were mixed with 50 µl of 3 mM p-nitrophenyl-α-D-glycopyranoside in 0.1 M sodium acetate pH 4.5 and incubated for 1 hour at 37° C. The reaction was stopped by addition of 150 µl of 0.1 M Tetraborate. The absorbance was measured at 405 nm. Aspergillus niger 70-56 was isolated from the well that showed high amyloglucoamylase activity.

Aspergillus niger 1-3-2 was constructed as follows. Approximately $1 \times 10^6$ protoplasts prepared from the mycelia of Aspergillus niger 70-56 were incubated with 2~3 µg of plasmid DNA of pToC103, harboring the Aspergillus nidulans amdS gene and amyloglucoamylase gene from Aspergillus niger under control of the TAKA amylase promoter from Aspergillus oryzae, and pHW454, containing an α-amylase gene from Aspergillus niger, in the presence of 36% polyethylene glycol and 10 mM CaCl for 20 minutes followed by the incubation with 55% polyethylene glycol for another 20 minutes. The protoplasts were regenerated on COVE medium with sucrose and colony 1-3-2 with increased amyloglucoamylase production was isolated. Subsequent Southern analysis on colony 1-3-2 showed that no part of either pToC103 or pHW454 was present in the genome of the colony.

Aspergillus niger genomic DNA was isolated from fungal mycelium for Southern hybridization, PCR, and genomic library constructions were carried out as followed: spores were inoculated in a shake flask containing 100 ml of PD medium and incubated at 34° C. for 4–5 days. Mycelia were harvested and washed in water. Then 0.5 ml of the mycelia were transferred into a 2 ml Eppendorf tube and dried in a Speed vac at 60° C. The dried mycelia were ground thoroughly followed by the addition of 0.5 ml of 50 mM EDTA pH 8.0, 0.2% SDS and 2 µl of DEP. The mixture was incubated at 65° C. for 20 minutes. Then 100 µl of 5 M potassium acetate pH 6.5 was added, mixed, incubated for 5 minutes on ice, and centrifuged at 12,000 × g for 15 minutes. A volume of 800 µl was transferred to a new tube, 2 µl of DEP was added, and incubated at 65° C. for 20 minutes. Then 600 µl of isopropanol was added, mixed, and centrifuged at 12,000 × g for 10 minutes. The supernatant was removed. The pellet was rinsed with cold 70% ethanol and resuspended in 100 µl of TE buffer.

A tripeptidyl aminopeptidase gene deletion cassette was constructed as follows. The Aspergillus niger tripeptidyl aminopeptidase gene was first cloned. From the first 30 amino acids of the N-terminal amino acid sequence, PCR primers were designed corresponding to DSIITP (5' primer) (SEQ ID NO. 23) and DYQADP (3' primer) (SEQ ID NO. 24). These primers were used for PCR of the Aspergillus niger genomic DNA with an annealing temperature of 42° C. The PCR products were electrophoresed on a 10% acrylamide gel. The fragments of the expected size of 65 bp were cloned using a TOPO TA Cloning Kit (Invitrogen, Carlsbad, Calif.) according to the manufacturer's instructions and sequenced. One clone had sequences that corresponded to the N-terminal amino acid sequence of *Aspergillus niger* tripeptidyl aminopeptidase.

In order to clone a larger DNA fragment encoding the tripeptidyl aminopeptidase, a primer #6010 (GCACTGTCTGAAGCAGCTGTACAACATCGGTG) (SEQ ID NO. 25) corresponding to the invariant N-terminal sequence was designed. From the internal amino acid sequence a PCR primer (degenerate 17-mers) corresponding to YAVYDK (3' primer, #5988) (SEQ ID NO. 26) was made. The degenerate primers were used for the PCR reactions using genomic *Aspergillus niger* DNA as the template with an annealing temperature of 45° C. The products were run on a 1% agarose gel and a fragment of approximately 950 bp was observed. Sequencing confirmed that the 950 bp fragment encoded the *Aspergillus niger* tripeptidyl aminopeptidase gene.

Genomic *Aspergillus niger* DNA was partially digested with the restriction enzyme Tsp509I and electrophoresed on a 0.7% agarose gel. Fragments between 2–6 kb were purified from the gel using a Qiaquick DNA gel extraction kit (QIAGEN, Valencia, Calif.) according to the manufacturer's instructions, and ligated into EcoRI arms of λZipLox as described by the manufacturer (GIBCO BRL, Life Technologies, Inc.). The genomic library was screened by excision of the genomic clones in pZL 1 from λZipLox phage as described by the manufacturer. The library was screened using the 950 bp tripeptidyl aminopeptidase gene fragment labeled with $\alpha$-$^{32}$P (Sambrook et al., 1989, Molecular Cloning: A Laboratory Manual ($2^{nd}$ edn.) Cold Spring Harbor Laboratory, Cold Spring Harbor, N.Y.). Several positives clones were identified and purified. Positive clones containing a 3.8 kb Tsp509I fragment was isolated and the plasmid was designated pJaL406.

The *Aspergillus niger* pyrG gene was cloned as follows. A library of *Aspergillus niger* Bo1 was created in EMBL4 according to manufacturer's instructions (Clontech, Palo Alto, Calif.). The library was screened with a dioxygenin-labeled PCR product. The primers were designed to the published *Aspergillus niger* sequence (accession no. X06626). The PCR reaction contained 2 μl of 10× Taq buffer, 2 μl of DIG labeling mix, 1μl of each primer, 50 ng of *Aspergillus ficium* pyrG, 2.5 units of Taq polymerase, and distilled water to 20 μl. The PCR reaction conditions and buffers were as described by the manufacturer (Boehringher Mannheim, Indianapolis, Ind.).

The dioxygenin-labeled fragment was used for hybridizations to the genomic library plaques using a modification of the Genius kit (Boehringher-Mannheim, Indianapolis, Ind.). The modification was the hybridization buffer and conditions were as described in Engler-Blum, 1993, Analytical Biochemistry 210: 235–244. Several EMBL4 clones that hybridized to the probe were identified from approximately 30,000 clones. Several positive clones were purified to homogeneity (Sambrook et al., 1989, supra), and phage DNA was isolated from the clones using the Qiagen lambda miniprep kit (Qiagen, Inc., Chatsworth, Calif.) according to the manufacturer's instructions. From one of the clones (7b) a Xba1 fragment of 4 kb containing the pyrG gene was subcloned into pUCI 118 to create pJRoy10.

The tripeptidyl aminopeptidase deletion plasmid pJaL462 was constructed as follows.

The tripeptidyl aminopeptidase plasmid pJaL406 was digested with XhoI, treated with bacterial alkaline phosphastase, and electrophoresed on a 0.7% agarose gel. The 7.0 kb fragment was purified using a Qiaquick DNA gel extraction kit. Plasmid pJRoy10 was digested with XhoI, and the 2.3 kb fragment encoding the *Aspergillus niger* pyrG gene was isolated by gel electrophoresis, and purified as described above.

The two fragments were mixed together and ligated. After transformation of *E. coli*, plasmid DNA was isolated from the clones using a Qiagen Miniprep kit (Qiagen, Inc., Chatsworth, Calif.) according to the manufacturer's instructions. The colonies carrying the correct plasmids were identified by restriction enzyme digestion of plasmid with XhoI. The correct clone pJaL462 consisted of pZL1 vector containing a fragment which carries the TPAP gene where the central XhoI fragment has been replaced with the 2.3 kb DNA fragment encoding the *Aspergillus niger* pyrG gene.

*Aspergillus niger* strain JaL303 was constructed as follows. *Aspergillus niger* PM8 is a spontaneously pyrG mutant of Aspergillus niger 1-3-2, which was selected for by growth on minimal medium 5FOA plates. The pyrG gene encodes orotidine 5'-phosphate carboxylase and mutants can be characterized as uridine auxotrophs. The identity of pyrG mutants was confirmed by complementation of growth on minimal medium with the *Aspergillus nidulans* pyrG gene.

The plasmid pJaL462 was linearized by SmaI and electrophoresed on a 0.7% agarose gel.

The linerarized plasmid was purified from the gel using a Qiaquick DNA gel extraction kit. The gel-purified fragment was used for the transformation of *Aspergillus niger* PM8 as described in Example 4 except that *Aspergillus niger* PM8 was grown overnight in YEG medium supplemented with 100 mM uridine. Transformants were selected for uridine prototrophy on minimal medium plates. A number of transformants were subsequently analyzed by Southern blotting and for tripeptidyl aminopeptidase activity U.S. Pat. No. 5,989,889. A transformant shown to have a 1.2 kb of XhoI fragment of the tripeptidyl aminopeptidase gene replaced by a 2.3 kbpyrG gene was selected and designated *Aspergillus niger* JaL303.

*Aspergillus niger* strain 303-10 was isolated as follows. *Aspergillus niger* 303-10 is a spontaneously caused pyrG mutant of *Aspergillus niger* JaL303, which was selected for growth of spores on a Minimal medium 5FOA plate. The pyrG gene encodes orotidine 5'-phosphate carboxylase and mutants can be characterized as uridine auxotrophs. The identity of pyrG mutants was confirmed by the complementation of the growth on a minimal medium with Aspergillus nidulans pyrG gene.

Example 8

Cloning of *Talaromyces emersonii* amyloglucosidase gene

PCR reactions using *Talaromyces emersonii* genomic DNA was performed with the primers 102435 and 117361 shown below.

Primer 102435: 5'-GTNCTNAAYAAYATHGG-3' (SEQ ID NO. 27)

Primer 117361: 3'-CTRAAYACCCTYCTYCA-5' (SEQ ID NO. 28)

PCR reactions were performed in a Hybaid thermocycler. The primers were added at 20 to 50 pmol each to 1 μg genomic DNA isolated as described in Example 7. Initial denaturation was for 5 minutes at 94° C. The amplification consisted of 30 cycles under the following conditions: denaturation for 1 minute at 94° C.; annealing for 1 minute at 40–55° C.; elongation for 2 minutes at 72° C. (5 minutes at last cycle). Four bands of 1400, 800, 650, and 525 bp were observed following electrophoresis on a 1%agarose gel. All four bands were purified from the gel using a Qiaquick DNA gel extraction kit and cloned into the vector pCR®2.1 (Invitrogen, Carlsbad, Calif.) according to the manufacturer's instructions. Sequencing of a few clones from each band and sequence comparisons to the *Aspergillus niger* amyloglucosidase revealed that a clone from the 650 bp band encoded for the N-terminal part of the *Talaromyces emersonii* amyloglucosidase. This clone was designated pJaL497.

To obtain more of the gene a specific primer (123036) was made from the sequence of clone pJaL497. The primers 123036 and 127420, shown below, were used for PCR of *Talaromyces emersonii* genomic DNA and a single fragment of 1500 bp was obtained using the conditions described above.

Primer 123036: 5'-GTGAGCCCAAGTTCAATGTG-3' (SEQ ID NO. 29)
Primer 127420: 3'-ACCCTYCTRCTRGGNTT-5' (SEQ ID NO. 30)

The PCR fragment was cloned into the pCR®2.1 following the manufacturer's protocols and sequenced. The sequence confirmed that this clone encoded for the *Talaromyces emersonii* amyloglucosidase. The clone was designated pJaL507.

The two clones pJaL497 and pJaL507 covered about 95% of the gene. In order to clone the missing part of the *Talaromyces emersonii* amyloglucosidase gene a genomic restriction map was constructed by using the two PCR fragments as probes to a Southern blot of *Talaromyces emersonii* genomic DNA digested with single or combination of a number of restriction enzymes.

A genomic library was constructed in Lambda ZAP II (Stratagene Cloning Systems, La Jolla, Calif.) according to the manufacturer's instructions following partial digestion of genomic DNA with EcoRI. Following digestion and electrophoreses on a 0.7% agarose gel, 4–7 kb fragments were purified from gel slices using a Qiaquick DNA gel extraction kit. The 4 to 7 kb fragments were ligated into Lambda ZAPII. For screening of the library In Vivo Excision (Mass Excision) of the phagemid from the Lambda ZAP II vector was performed according to the manufacturer instructions (Stratagene Cloning Systems, La Jolla, Calif.). Colony hybridization of approximately 25,000 colonies was conducted as described in Sambrook et al., 1989, supra. $^{32}$P-labelled probes of the 0.7 kb EcoRI fragment from pJaL497and the 0.75 kb EcoRV fragment from pJaL507 encoding the N-terminal half and the C-terminal half of the *Talaromyces emersonii* amyloglucosidase, respectively. The library was first screened using the 0.7 kb EcoRI fragment from pJaL497 (encoding the N-terminal half of the amyloglucosidase gene) as a probe to obtain the start of the amyloglucosidase gene. One clone was obtained and designated pJaL511. In a second screening of the library a 0.75 kb EcoRV fragment from pJaL507, encoding the C-terminal half of the amyloglucosidase gene, was used as a probe to obtain the missing C-terminal of the amyloglucosidase gene. One clone was obtained and designated pJaL510.

The coding region of the *Talaromyces emersonii* amyloglucosidase gene was PCR amplified from genomic DNA with the primers 139746 and 139747 shown below using the conditions described above.

```
Primer 139746: 5'-GACAGATCTCCACCATGGCGTCCCTCGTTG   (SEQ ID NO. 31)
                     BglII
Primer 139747: 5'-GACCTCGAGTCACTGCCAACTATCGTC      (SEQ ID NO. 32)
                     XhoI
```

A portion of the PCR reaction was run on a 1% agarose gel. The expected PCR product of 2099 bp was observed. This fragment was purified, digested with BglII and XhoI, and cloned into the BamHI and XhoI sites in an Aspergillus expression cassette containing the NA2-tpi promoter and AMG terminator and *Aspergillus nidulans* amdS gene.

A clone pJaL519 was isolated and sequenced to confirm that no changes had occurred in the amyloglucosidase gene sequence. In pJaL518 a silent mutation of Glu-593, GAA to GAG, was found.

Example 9

Figure 8:
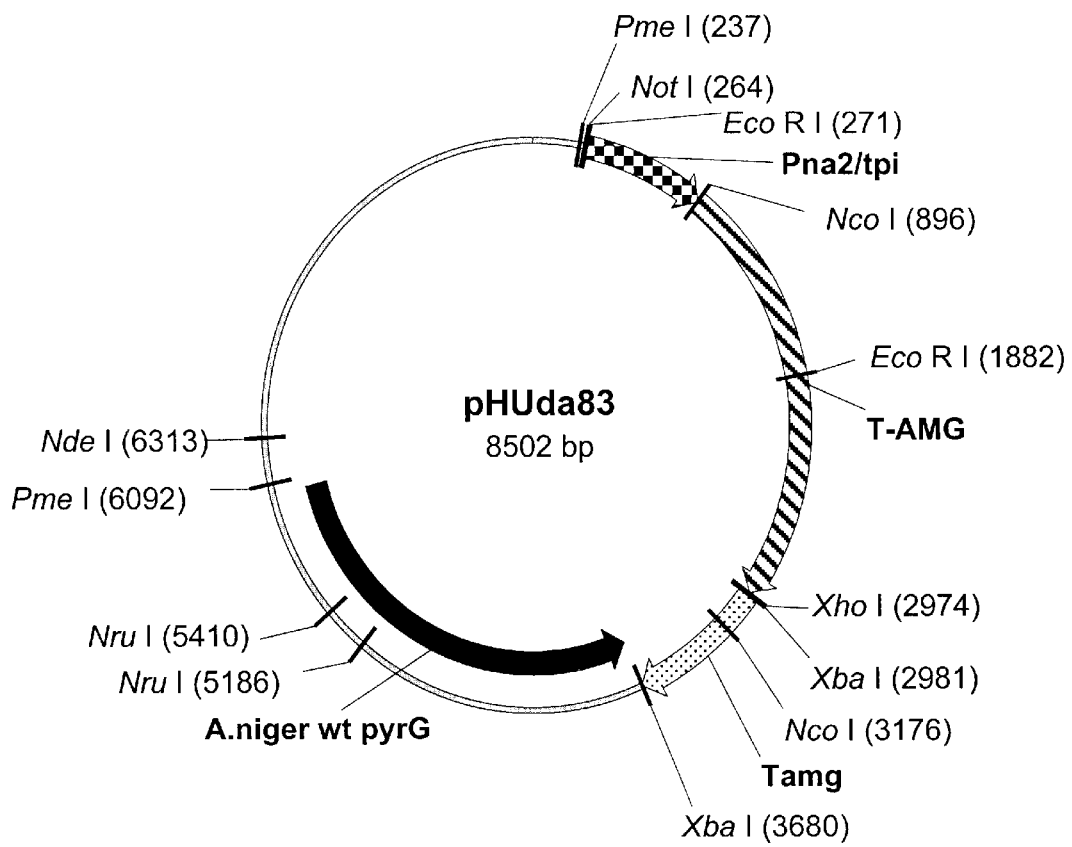
FIG. 8 shows a restriction map of pHUda83.
Figure 9:
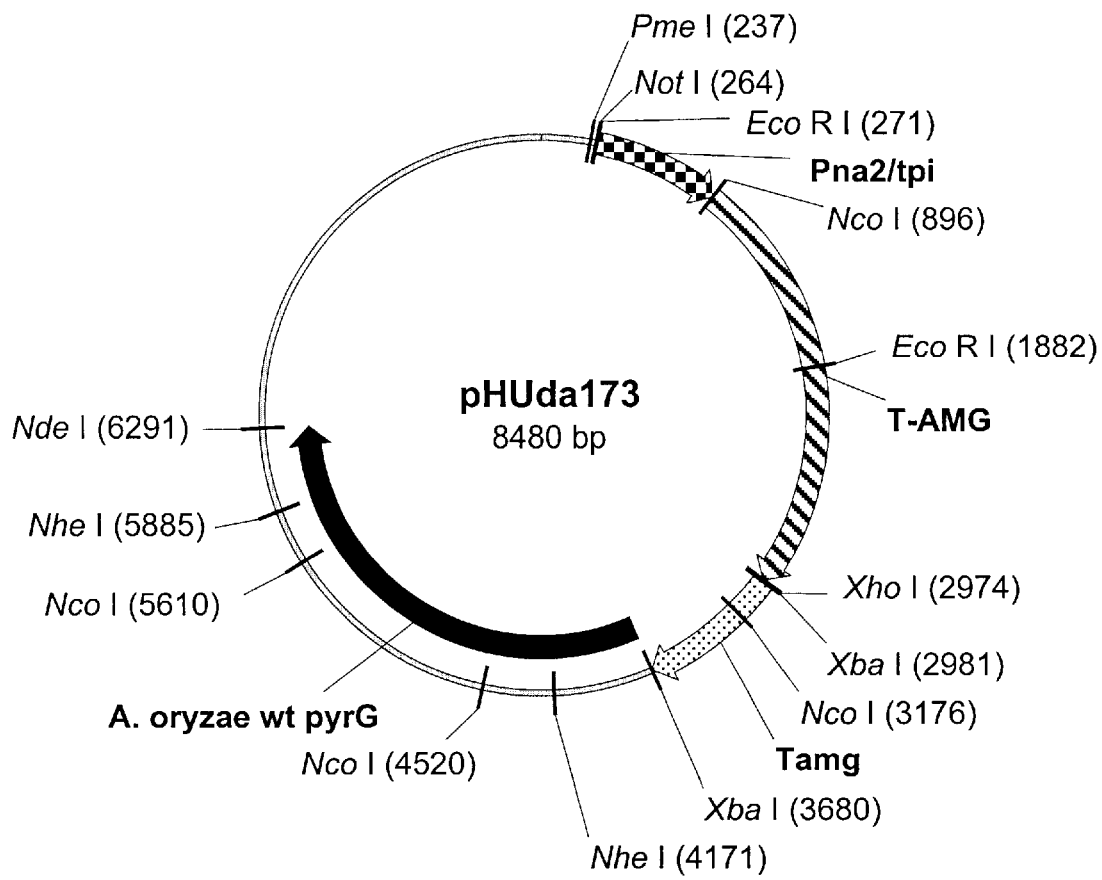
FIG. 9 shows a restriction map of pHUda173.
Figure 10:
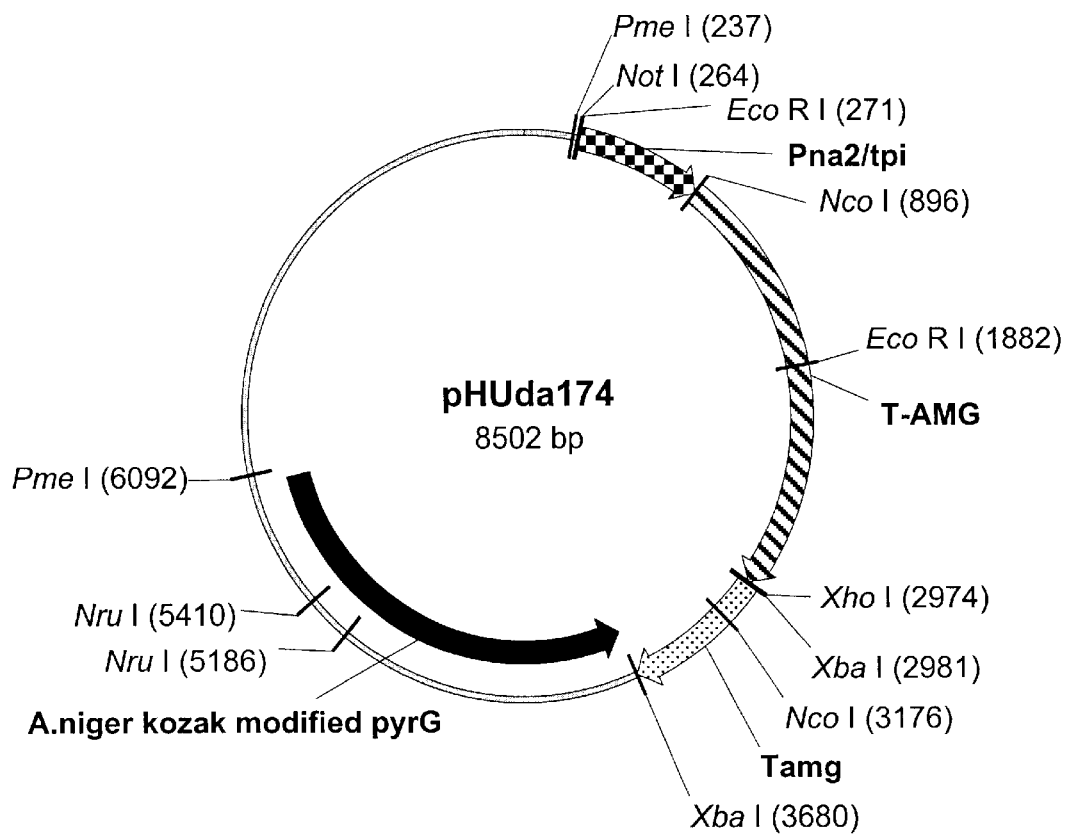
FIG. 10 shows a restriction map ofpHUda174.

Construction of *Talaromyces emersonii* Amyloglucosidase Expression Vectors pHUda83 (FIG. 8) was constructed as follows. The 3.4 kb *Talaromyces emersonii* amyloglucosidase gene, including the NA2/TPI promoter and amyloglucosidase terminator, was isolated from pJaL518. pJal518 was digested with NotI and XbaI and electrophoresed on a 1% agrarose gel to isolate the 3.4 kb fragment. The fragment was purified from the gel using the Qiaquick DNA gel extraction kit. pHUda83 was made by inserting the 3.5 kb fragment into NotI and XbaI digested pHUda15 which contained the *Aspergillus niger* pyrG gene. Following transformation of *E. coli*, plasmid DNA was isolated from colonies using a Qiagen Miniprep kit. Clones were analyzed by digestion with NotI and XbaI followed by electrophoreses on a 1% agarose gel to confirm the correct clones.

pHUda173 (FIG. 9) was constructed as follows. The *Aspergillus niger* pyrG gene in pHUda83 was removed by digesting with XbaI and NdeI and electrophoresed on a 1% agarose gel. The 5.4 kb fragment was purified using a Qiaquick DNA gel extraction kit. The 2.6 kb *Aspergillus oryzae* pyrG gene was isolated from pHUda132 digested with XbaI and NdeI following electrophoresis on a 1% agarose gel and purified with a Qiaquick DNA gel extraction kit. pHUda173 was created by ligating the 2.6 kb *Aspergillus oryzae* pyrG fragment with the 5.4 kb *Aspergillus niger* pyrG gene deleted pHUda83. Following transformation in *E. coli*, plasmid DNA was isolated using a Qiagen Miniprep kit. The plasmids were analyzed by digestion with XbaI and NdeI followed by electrophoresis on a 1% agarose gel.

pHUda174 (FIG. 10) was constructed as follows. The 220 bp fragment containing the N-terminal of the *Aspergillus niger* pyrG gene was removed from pHUda83 by NruI digestion. pHUda83 was digested with NruI and electrophoresed on a 0.7% agarose gel. The 8.3 kb fragment was purified using a Qiaquick DNA gel extraction kit.

PCR reactions for making modified Kozak sequences of the *Aspergillus niger* pyrG gene were conducted with the primers HU281 and HU282 shown below.

```
Primer HU281 (SEQ ID NO. 33):
5'-AGGTCAATCGCGACTTGGAGGACATAAAACTGATGGAGGGGTTAA-3'
         NruI Primer HU282 (SEQ ID NO. 34):
5'-TGGAGGGGCTCGCGATGATTTTAC-3'
          NruI
```

Figure 11:
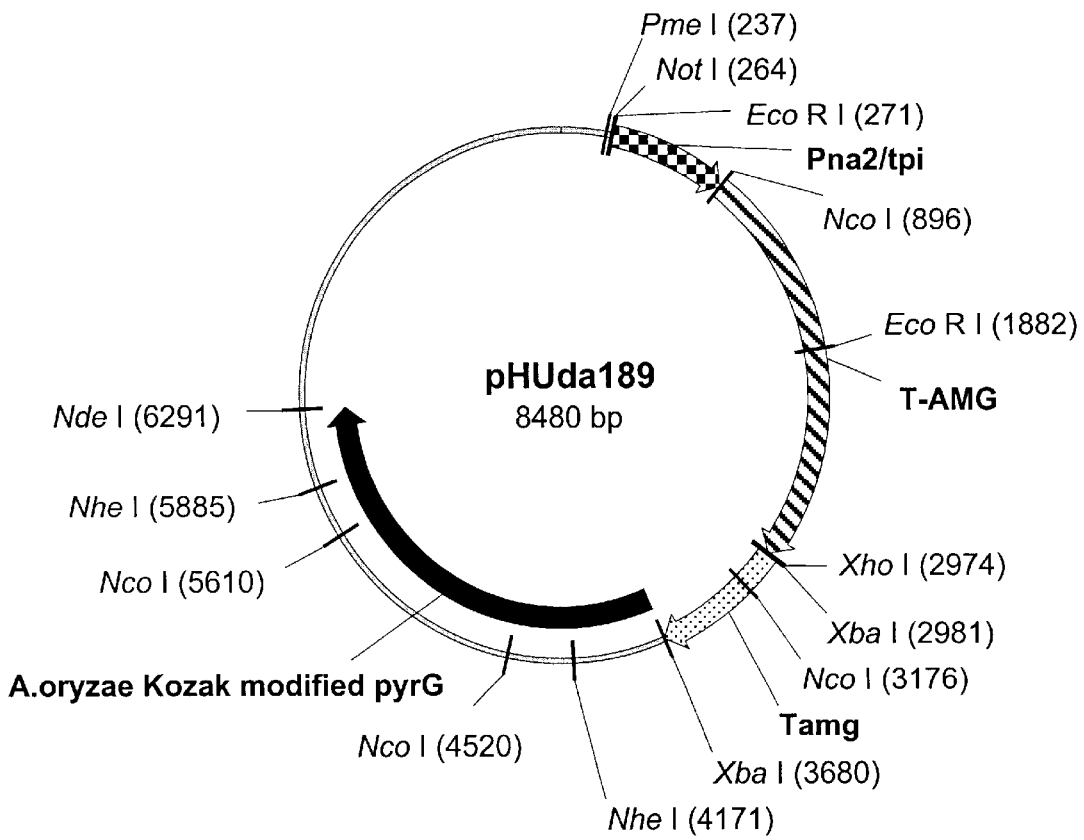
FIG. 11 shows a restriction map of pHUda189.

The primers were added at 20 to 50 pmol each to 0.1 μg of pHUda83. Initial denaturation was for 5 minutes at 94° C. The amplification consisted of 30 cycles under the following conditions: denaturation for 1 minute at 94° C.; annealing for 1 minute at 40–55° C.; and elongation for 2 minutes at 72° C. (5 minutes at last cycle). A portion of the PCR reaction was run on a 1.5% agarose gel. The expected PCR product of 220 bp was observed. This fragment was purified using a Qiaquick DNA gel extraction kit, digested with NruI, and cloned into the 8.3 kb fragment of pHUda83 after alkaline phosphatase treatment. Plasmid DNA of a clone was isolated following transformation of *E. coli* and sequenced to confirmed that no changes had occurred in the pyrG sequences except for the changes in the Kozak region positions (acaccATG to gttttATG). The resultant plasmid was designated pHUda174.

pHUda189 (FIG. 11) was constructed as follows. The 490 bp fragment containing the 5' portion of the *Aspergillus oryzae* pyrG gene was removed from pHUda173 by NheI partial digestion and XbaI digestion. Following digestion of the plasmid DNA with the restriction enzymes and electrophoresis on a 0.7% agarose gel, the fragment of approximately 7.9 kb was purified from the gel using a Qiaquick DNA gel extraction kit.

PCR reactions for making the modified Kozak sequences of the *Aspergillus oryzae* pyrG gene were conducted with the primers HU64 and HU298 shown below.

```
Primer HU64:
5'-TAAATCCGATCATTGATCCACCGCCCACGA-3'                                          (SEQ ID NO.35)

Primer HU298:
         NheI
5'-TGCTTGCTAGCGCGTGCGCTGTAGGTCAATTGCGACTTGGAAGACATAAAACCGATGGAGGGGTAGCG-3'   (SEQ ID NO.36)
```

The primers were added at 20 to 50 pmol each to 0.1 μg of pHUda173. Initial denaturation was for 5 minutes at 94° C. The amplification consisted of 30 cycles under the following conditions: denaturation for 1 minute at 94° C.; annealing for 1 minute at 40–55° C.; and elongation for 2 minutes at 72° C. (5 minutes at last cycle). A portion of the PCR reaction was run on a 1.5% agarose gel. Only the expected PCR product on 490 bp was seen. This fragment was purified, digested with XbaI and NheI, and ligated into the 7.9 kb XbaI/NheI (partial) digested pHUda173 fragment. Plasmid DNA of a clone was isolated following transformation of *E. coli* and sequenced to confirmed that no changes had occurred in the pyrG sequences except for the changes in the Kozak region positions (ccaccATG to gttttATG). The resultant plasmid was designated pHUda189.

Example 10

Transformation of *Aspergillus niger* JaL303-10

*Aspergillus niger* JaL303-10 was transformed with pHUda83, pHUda173, pHUda174, or pHUda189 as described in Example 4 except prior to protoplast preparation the strain was grown overnight in YEG medium supplemented with 100 mM uridine. Transformants were selected by growth on minimal medium plates with sucrose. Twenty tranformants with each vector were isolated and purified twice by spreading of spores on minimal medium plates followed by isolation of a single colony.

Example 11

Amyloglucosidase Expression of the *Aspergillus niger* JaL303-10 Transformants

Strains were cultivated on slants for 7–21 days at 32° C. and inoculated to MLC medium (100 ml MLC in 250 ml glass flask with baffles). Cultivation was at 32° C. for 2 days at 230 rpm. After 2 days, 10% of the seed culture was transferred into MU-1 medium (100 ml in 250 ml baffled flasks) and cultivation was at 32° C. for 7 days 230 rpm.

Culture supernatants from the transformants were analyzed using Rocket Immuno Electrophoresis (RIE) as described by N. H. Axelsen, J. Krøll, and B. Weeks, editors,

*A Manual of Quantitative Immunoelectrophoresis*, Blackwell Scientific Publications, 1973. RIE is specially modified in order to quantify antigen concentration. When an electric field is applied, most protein antigens migrate into an agar gel containing antibody. Antibody proteins tend to migrate towards the cathode. When they meet antigens, they will form antigen-antibody complex. In antibody or antigen excess, these complex are soluble, but near the equivalence point precipitate complexes are formed having a 'rocket' shape. As more antigen reaches the rocket, the precipitate redissolves and migrates further towards the anode. Eventually, when no more antigens remain to migrate, the rocket becomes stationary and stable. The area of gel beneath the rocket is proportional to the antigen concentration.

Polyclonal antibody was mixed with agarose solution before samples were applied. A 750 µl volume of T-AMG antibody was added to 100 ml of 1% agarose. Then 10 µl of each sample was applied to the gel containing the T-AMG antibody. The detection range of the T-AMG antibody was 0.5–3.0 AG per ml.

Results are shown in the Table 3 below.

TABLE 3

Amyloglucosidase Expression in Transformants

| Plasmid | Kozak Sequence | Relative Best Yield of AMG | Average of Five Best Yields |
|---|---|---|---|
| pHUda83 | acaccATG (wt) | 1.0 | 1.0 |
| pHUda174 | gttttATG (crippled) | 2.46 | 5.1 |
| pHUda173 | ccaccATG (wt) | 2.11 | 3.16 |
| pHUda189 | gttttATG (crippled) | 3.44 | 6.70 |

TABLE 3-continued

Amyloglucosidase Expression in Transformants

All yields are relative to those of the pHUda83 transformants. Amyloglucosidase yields were higher in transformants containing the crippled Kozak sequence than in those containing the *Aspergillus niger* wild-type Kozak sequence (pHUda174 versus pHUda83). Amyloglucosidase yields were also higher in transformants containing the crippled Kozak sequence than in those containing the *Aspergillus oryzae* wild-type Kozak sequence (pHUda173 versus pHUda189).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a polypeptide, comprising: (a) cultivating a fungal host cell in a medium conducive for the production of the polypeptide; and (b) isolating the polypeptide from the cultivation medium; wherein the fungal host cell comprises a nucleic acid construct comprising in tandem a first nucleic acid sequece encoding the polypeptide and a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, the crippled translational initiator sequence comprises a T at the −3 position and a T at one or more of the −1, −2, and −4 positions, and the copy number of the first nucleic acid sequence has been increased by culturing the cell under conditions that select for multiple copies of the selectable marker.

2. The method of claim 1, wherein the first nucleic acid sequence encodes a polypeptide native to the fungal host cell.

3. The method of claim 1, wherein the first nucleic acid sequence encodes a polypeptide heterologous to the fungal host cell.

4. The method of claim 1, wherein the polypeptide is a hormone, enzyme, receptor or portion thereof, antibody or portion thereof, or reporter.

5. The method of claim 4, wherein the enzyme is an oxidoreductase, transferase, hydrolase, lyase, isomerase, or ligase.

6. The method of claim 5, wherein the enzyme is an aminopeptidase, amylase, carbohydrase, carboxypeptidase, catalase, cellulase, chitinase, cutinase, cyclodextrin glycosyltransferase, deoxyribonuclease, esterase, aipha-galactosidase, beta-galactosidase, glucoamylase, alpha-glucosidase, beta-glucosidase, invertase, laccase, lipase, mannosidase, mutanase, oxidase, a pectinolytic enzyme, peroxidase, phytase, polyphenoloxidase, proteolytic enzyme, ribonuclease, transglutaminase, or xylanase.

7. The method of claim 1, wherein the selectable marker is selected from the group consisting of ADE2, HIS3, LEU2, LYS2, MET3, TRP1, URA3, amdS, argB, bar, hygB, niaD, pyrG, sC, and trpC.

8. The method of claim 1, wherein the nucleic acid construct is contained in the chromosome of the fungal host cell.

9. The method of claim 1, wherein the nucleic acid construct is contained on an extrachromosomal element.

10. The method of claim 1, wherein the fungal host cell is a filamentous fungal or yeast cell.

11. The method of claim 10, wherein the filamentous fungal cell is an Acremonium, Aspergillus, Fusarium, Humicola, Mucor, Myceliophthora, Neurospora, Penicillium, Thielavia, Tolypocladium, or Trichoderma cell.

12. The method of claim 10, wherein the yeast cell is a Candida, Hansenula, Kluyveromyces, Pichia, Saccharomyces, Schizosaccharomyces, or Yarrowia cell.

13. The method of claim 10, wherein the filamentous fungal host cell is an Aspergillus cell.

14. The method of claim 10, wherein the filamentous fungal host cell is a Fusarium cell.

15. The method of claim 1, wherein the fungal host cell produces at least about 25% more polypeptide relative to a fungal cell containing a native translational initiator sequence operably linked to a nucleic acid sequence encoding the polypeptide when cultured under the same conditions.

16. A nucleic acid construct comprising in tandem a first nucleic acid sequence encoding a polypeptide and a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, wherein the crippled translational initiator sequence comprises a T at the −3 position and a T at one or more of the −1, −2, and −4 positions.

17. A recombinant expression vector, comprising the nucleic acid construct of claim 16.

18. A recombinant fungal host cell, comprising the nucleic acid construct of claim 16.

19. The recombinant fungal host cell of claim 18, wherein the fungal host cell is a filamentous fungal or yeast cell.

20. The recombinant fungal host cell of claim 19, wherein the filamentous fungal cell is an Acremonium, Aspergillus, Fusarium, Humicola, Mucor, Myceliophthora, Neurospora, Penicillium, Thielavia, Tolypocladium, or Trichoderma cell.

21. The recombinant fungal host cell of claim 19, wherein the yeast cell is a Candida, Hansenula, Kluyveromyces, Pichia, Saccharomyces, Schizosaccharomyces, or Yarrowia cell.

22. The recombinant fungal host cell of claim 19, wherein the filamentous fungal host cell is an Aspergillus cell.

23. The recombinant fungal host cell of claim 19, wherein the filamentous fungal host cell is a Fusarium cell.

24. A fungal host cell comprising a first nucleic acid sequence encoding a polypeptide in tandem with a second nucleic acid sequence comprising a crippled translational initiator sequence operably linked to a gene encoding a selectable marker in which the 3' end of the crippled translational initiator sequence is immediately upstream of the initiator codon of the gene encoding the selectable marker, wherein the copy number of the first nucleic acid sequence has been increased by culturing the cell under conditions that select for multiple copies of the selectable marker, wherein the crippled translational initiator sequence comprises a T at the −3 position and a T at one or more of the −1, −2, and −4 positions.

* * * * *

SEQUENCE LISTING

```
<160> NUMBER OF SEQ ID NOS: 36

<210> SEQ ID NO 1
<211> LENGTH: 21
<212> TYPE: DNA
<213> ORGANISM: Aspergillus oryzae

<400> SEQUENCE: 1
tggtgtacag gggcataaaa t                                         21

<210> SEQ ID NO 2
<211> LENGTH: 34
<212> TYPE: DNA
<213> ORGANISM: Aspergillus oryzae

<400> SEQUENCE: 2
atttaaatcc agttgtgtat atagaggatt gtgg                           34

<210> SEQ ID NO 3
<211> LENGTH: 30
<212> TYPE: DNA
<213> ORGANISM: Aspergillus oryzae

<400> SEQUENCE: 3
atttaaatga tgaggagctc ccttgtgctg                                30

<210> SEQ ID NO 4
```

```
<211> LENGTH: 29
<212> TYPE: DNA
<213> ORGANISM: Aspergillus oryzae

<400> SEQUENCE: 4
ttaattaact agagtcgacc cagccgcgc                                      29

<210> SEQ ID NO 5
<211> LENGTH: 33
<212> TYPE: DNA
<213> ORGANISM: Aspergillus oryzae

<400> SEQUENCE: 5
cattggagaa ccgccgtcat gtcttcgaag tcc                                 33

<210> SEQ ID NO 6
<211> LENGTH: 33
<212> TYPE: DNA
<213> ORGANISM: Aspergillus oryzae

<400> SEQUENCE: 6
ggacttcgaa gacatgacgg cggttctcca atg                                 33

<210> SEQ ID NO 7
<211> LENGTH: 33
<212> TYPE: DNA
<213> ORGANISM: Aspergillus oryzae

<400> SEQUENCE: 7
cattggagaa ccgccctcat gtcttcgaag tcc                                 33

<210> SEQ ID NO 8
<211> LENGTH: 33
<212> TYPE: DNA
<213> ORGANISM: Aspergillus oryzae

<400> SEQUENCE: 8
ggacttcgaa gacatgaggg cggttctcca atg                                 33

<210> SEQ ID NO 9
<211> LENGTH: 33
<212> TYPE: DNA
<213> ORGANISM: Aspergillus oryzae

<400> SEQUENCE: 9
cattggagaa ccgccttcat gtcttcgaag tcc                                 33

<210> SEQ ID NO 10
<211> LENGTH: 33
<212> TYPE: DNA
<213> ORGANISM: Aspergillus oryzae

<400> SEQUENCE: 10
ggacttcgaa gacatgaagg cggttctcca atg                                 33

<210> SEQ ID NO 11
<211> LENGTH: 33
<212> TYPE: DNA
<213> ORGANISM: Aspergillus oryzae

<400> SEQUENCE: 11
cattggagaa ccggttttat gtcttcgaag tcc                                 33
```

```
<210> SEQ ID NO 12
<211> LENGTH: 33
<212> TYPE: DNA
<213> ORGANISM: Aspergillus oryzae

<400> SEQUENCE: 12
ggacttcgaa gacataaaac cggttctcca atg                         33

<210> SEQ ID NO 13
<211> LENGTH: 21
<212> TYPE: DNA
<213> ORGANISM: Aspergillus oryzae

<400> SEQUENCE: 13
aatgatagtc gggttcgtga c                                      21

<210> SEQ ID NO 14
<211> LENGTH: 21
<212> TYPE: DNA
<213> ORGANISM: Aspergillus oryzae

<400> SEQUENCE: 14
tatcctggag gggcattggt g                                      21

<210> SEQ ID NO 15
<211> LENGTH: 19
<212> TYPE: DNA
<213> ORGANISM: Aspergillus oryzae

<400> SEQUENCE: 15
ccggaatgtt aggctggtt                                         19

<210> SEQ ID NO 16
<211> LENGTH: 20
<212> TYPE: DNA
<213> ORGANISM: Aspergillus oryzae

<400> SEQUENCE: 16
ttctttgtct ctgcgtggac                                        20

<210> SEQ ID NO 17
<211> LENGTH: 26
<212> TYPE: DNA
<213> ORGANISM: Aspergillus oryzae

<400> SEQUENCE: 17
tggccagtcc tattcgtcga gaggtc                                 26

<210> SEQ ID NO 18
<211> LENGTH: 23
<212> TYPE: DNA
<213> ORGANISM: Aspergillus oryzae

<400> SEQUENCE: 18
ctcccttgtg ctgttctttg tct                                    23

<210> SEQ ID NO 19
<211> LENGTH: 25
<212> TYPE: DNA
<213> ORGANISM: Aspergillus oryzae

<400> SEQUENCE: 19
ctgtgcaaag agattgaact ggtta                                  25
```

-continued

```
<210> SEQ ID NO 20
<211> LENGTH: 20
<212> TYPE: DNA
<213> ORGANISM: Aspergillus oryzae

<400> SEQUENCE: 20
tgggtatggg ttccgccgcc                                               20

<210> SEQ ID NO 21
<211> LENGTH: 21
<212> TYPE: DNA
<213> ORGANISM: Aspergillus oryzae

<400> SEQUENCE: 21
gatggtccag gtctcccaga a                                             21

<210> SEQ ID NO 22
<211> LENGTH: 17
<212> TYPE: DNA
<213> ORGANISM: Aspergillus oryzae

<400> SEQUENCE: 22
cagggttgcg ggagaca                                                  17

<210> SEQ ID NO 23
<211> LENGTH: 6
<212> TYPE: PRT
<213> ORGANISM: Aspergillus oryzae

<400> SEQUENCE: 23

Asp Ser Ile Ile Thr Pro
 1               5

<210> SEQ ID NO 24
<211> LENGTH: 6
<212> TYPE: PRT
<213> ORGANISM: Aspergillus oryzae

<400> SEQUENCE: 24

Asp Tyr Gln Ala Asp Pro
 1               5

<210> SEQ ID NO 25
<211> LENGTH: 32
<212> TYPE: DNA
<213> ORGANISM: Aspergillus oryzae

<400> SEQUENCE: 25
gcactgtctg aagcagctgt acaacatcgg tg                                 32

<210> SEQ ID NO 26
<211> LENGTH: 6
<212> TYPE: PRT
<213> ORGANISM: Aspergillus oryzae

<400> SEQUENCE: 26

Tyr Ala Val Tyr Asp Lys
 1               5

<210> SEQ ID NO 27
<211> LENGTH: 17
<212> TYPE: DNA
<213> ORGANISM: Aspergillus oryzae
<220> FEATURE:
```

-continued

```
<223> OTHER INFORMATION: n = a, c, g or t
<223> OTHER INFORMATION: y = t or c
<223> OTHER INFORMATION: h = a, c or t

<400> SEQUENCE: 27
gtnctnaaya ayathgg                                                  17

<210> SEQ ID NO 28
<211> LENGTH: 17
<212> TYPE: DNA
<213> ORGANISM: Aspergillus oryzae
<220> FEATURE:
<223> OTHER INFORMATION: r = g or a
<223> OTHER INFORMATION: y = t or c

<400> SEQUENCE: 28
ctraayaccc tyctyca                                                  17

<210> SEQ ID NO 29
<211> LENGTH: 20
<212> TYPE: DNA
<213> ORGANISM: Aspergillus oryzae

<400> SEQUENCE: 29
gtgagcccaa gttcaatgtg                                               20

<210> SEQ ID NO 30
<211> LENGTH: 17
<212> TYPE: DNA
<213> ORGANISM: Aspergillus oryzae
<220> FEATURE:
<223> OTHER INFORMATION: y = t or c
<223> OTHER INFORMATION: r = g or a
<223> OTHER INFORMATION: n = a, c, g or t

<400> SEQUENCE: 30
accctyctrc trggntt                                                  17

<210> SEQ ID NO 31
<211> LENGTH: 30
<212> TYPE: DNA
<213> ORGANISM: Aspergillus oryzae

<400> SEQUENCE: 31
gacagatctc caccatggcg tccctcgttg                                    30

<210> SEQ ID NO 32
<211> LENGTH: 27
<212> TYPE: DNA
<213> ORGANISM: Aspergillus oryzae

<400> SEQUENCE: 32
gacctcgagt cactgccaac tatcgtc                                       27

<210> SEQ ID NO 33
<211> LENGTH: 45
<212> TYPE: DNA
<213> ORGANISM: Aspergillus oryzae

<400> SEQUENCE: 33
aggtcaatcg cgacttggag gacataaaac tgatggaggg gttaa                   45

<210> SEQ ID NO 34
<211> LENGTH: 24
<212> TYPE: DNA
```

-continued

```
<213> ORGANISM: Aspergillus oryzae

<400> SEQUENCE: 34
tggaggggct cgcgatgatt ttac                                          24

<210> SEQ ID NO 35
<211> LENGTH: 30
<212> TYPE: DNA
<213> ORGANISM: Aspergillus oryzae

<400> SEQUENCE: 35
taaatccgat cattgatcca ccgcccacga                                    30

<210> SEQ ID NO 36
<211> LENGTH: 68
<212> TYPE: DNA
<213> ORGANISM: Aspergillus oryzae

<400> SEQUENCE: 36
tgcttgctag cgcgtgcgct gtaggtcaat tgcgacttgg aagacataaa accgatggag   60
gggtagcg                                                            68
```